(12) United States Patent
Hikage et al.

(10) Patent No.: US 8,969,100 B2
(45) Date of Patent: Mar. 3, 2015

(54) METHOD FOR DETECTING AFFERENT LYMPH VESSEL INFLOW REGIONS AND METHOD FOR IDENTIFYING SPECIFIC CELLS

(75) Inventors: Makoto Hikage, Miyagi (JP); Kohsuke Gonda, Miyagi (JP); Motohiro Takeda, Miyagi (JP); Takashi Kamei, Miyagi (JP); Noriaki Ohuchi, Miyagi (JP); Hideki Gouda, Tokyo (JP); Yasushi Nakano, Tokyo (JP)

(73) Assignees: Tohoku University, Miyagi (JP); Konica Minolta Medical & Graphic, Inc., Tokyo (JP)

( * ) Notice: Subject to any disclaimer, the term of this patent is extended or adjusted under 35 U.S.C. 154(b) by 390 days.

(21) Appl. No.: 13/379,320
(22) PCT Filed: Mar. 11, 2010
(86) PCT No.: PCT/JP2010/054083
§ 371 (c)(1), (2), (4) Date: Dec. 19, 2011
(87) PCT Pub. No.: WO2010/150578
PCT Pub. Date: Dec. 29, 2010

(65) Prior Publication Data
US 2012/0107831 A1    May 3, 2012

(30) Foreign Application Priority Data
Jun. 26, 2009 (JP) .................................. 2009-152781

(51) Int. Cl.
G01N 33/543 (2006.01)
G01N 33/574 (2006.01)
(Continued)

(52) U.S. Cl.
CPC ........ *G01N 21/6458* (2013.01); *A61K 49/0017* (2013.01); *A61K 49/0067* (2013.01);
(Continued)

(58) Field of Classification Search
USPC .......... 435/7.2, 7.23, 7.24, 40.52, 287.2, 372; 436/518, 523, 524, 528, 546, 56, 63, 436/64, 164, 172; 422/82.03; 424/9.3
See application file for complete search history.

(56) References Cited

U.S. PATENT DOCUMENTS

2007/0232904 A1* 10/2007 Kitayama .................... 600/431
2008/0102036 A1*  5/2008 Poss et al. ................... 424/9.6

FOREIGN PATENT DOCUMENTS

JP    2004-269439    9/2004
JP    2006-014868    1/2006
JP    2009-190976    8/2009

OTHER PUBLICATIONS

Ballou et al. Sentinel Lymph Node Imaging Using Quantum Dots in Mouse Tumor Models, Bioconjugate Chem 18: 389-396 (2007).*
Frangioni et al. Sentinel Lymph Node Mapping with Type II Quantum Dots, Methods Mol. Biol. 374: 147-159 (2007).*
Diaz et al. Histologic Localization of Sentinel Lymph Node Metastases in Breast Cancer, The American Journal of Surgical Pathology 27 (3): 385-389 (2003).*
Sentinel node biopsy in breast cancer, Kazuyoshi Motomura, pp. 475-485, Abstract p. 475.
Sentinel Lymph Node Imaging Using Quantum Dots in Mouse Tumor Models, Byron Ballou, pp. 389-396.
(Continued)

*Primary Examiner* — Gail R Gabel
(74) *Attorney, Agent, or Firm* — Lucas & Mercanti, LLP

(57) ABSTRACT

Regions where metastatic cancer cells can exist are detected with high accuracy in a sentinel lymph node. Quantum dots are injected into the vicinity of a cancer in a living body, thereby identifying the location of the sentinel lymph node by means of fluorescence. Subsequently, the sentinel lymph node is extracted. With respect to the sentinel lymph node extracted with quantum dots injected, structural analysis is conducted by means of precision fluorescence measurement which uses a confocal fluorescence microscope for monomolecular observation. Specifically, the fluorescence intensity is measured with respect to each of multiple areas in the sentinel lymph nodes, and out of the multiple areas measured, one or more areas are detected as afferent lymph vessel inflow regions in descending order of fluorescence intensity.

15 Claims, 31 Drawing Sheets

(51) Int. Cl.
  *G01N 21/64* (2006.01)
  *A61K 49/00* (2006.01)
  *B82Y 5/00* (2011.01)
  *B82Y 15/00* (2011.01)
  *G01N 33/58* (2006.01)
  *A61B 5/00* (2006.01)

(52) U.S. Cl.
  CPC  *B82Y 5/00* (2013.01); *B82Y 15/00* (2013.01); *G01N 33/57492* (2013.01); *G01N 33/588* (2013.01); *A61B 5/0071* (2013.01); *A61B 5/41* (2013.01); *G01N 2201/0221* (2013.01)
  USPC ...... 436/523; 435/7.23; 435/7.24; 435/40.52; 435/287.2; 435/372; 436/518; 436/546; 436/56; 436/63; 436/64; 436/164; 436/172; 424/9.3; 422/82.03

(56) References Cited

OTHER PUBLICATIONS

JACS Articles, Sang-Wook Kim, J. Am. Chem. Soc. 2005, 127, 10526-10532.
Canceer Research, Tohru Hoshida, et al, first page and pp. 8065-8075.
Sentinel node biopsy in breast cancer, Kazuyoshi Motomura, pp. 475-485, (Mar. 2006).
Sentinel Lymph Node Imaging Using Quantum Dots in Mouse Tumor Models, Byron Ballou, pp. 389-396, (2007).
JACS Articles, Sang-Wook Kim, J. Am. Chem. Soc. 2005, 127, 10526-10532, (2005).
Canceer Research, Tohru Hoshida, et al, first page and pp. 8065-8075, (2006).

* cited by examiner

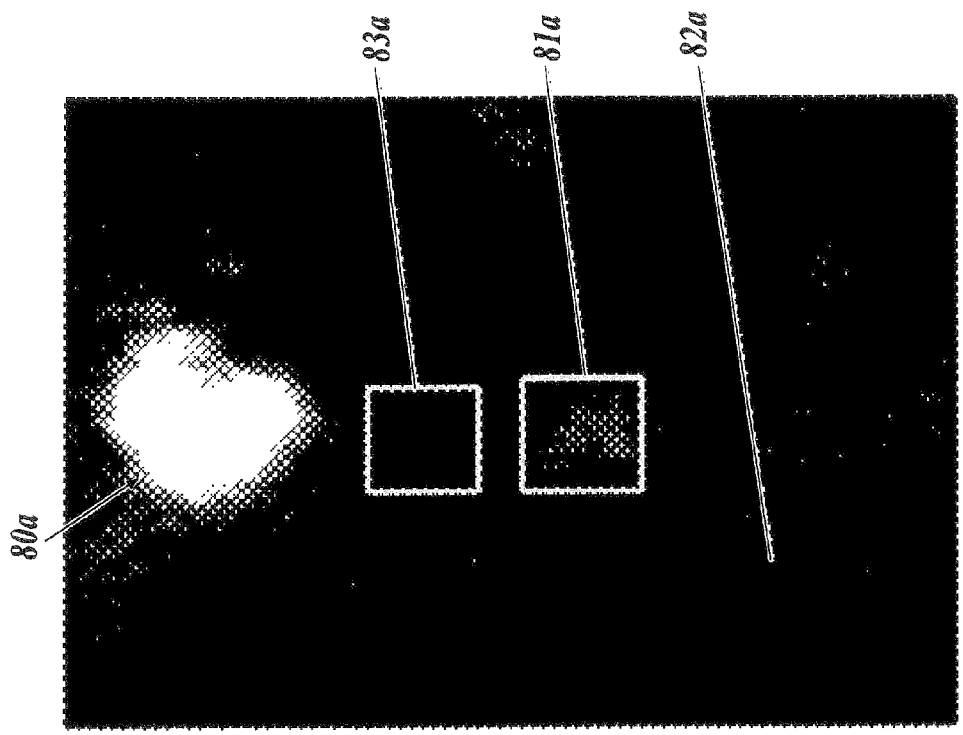
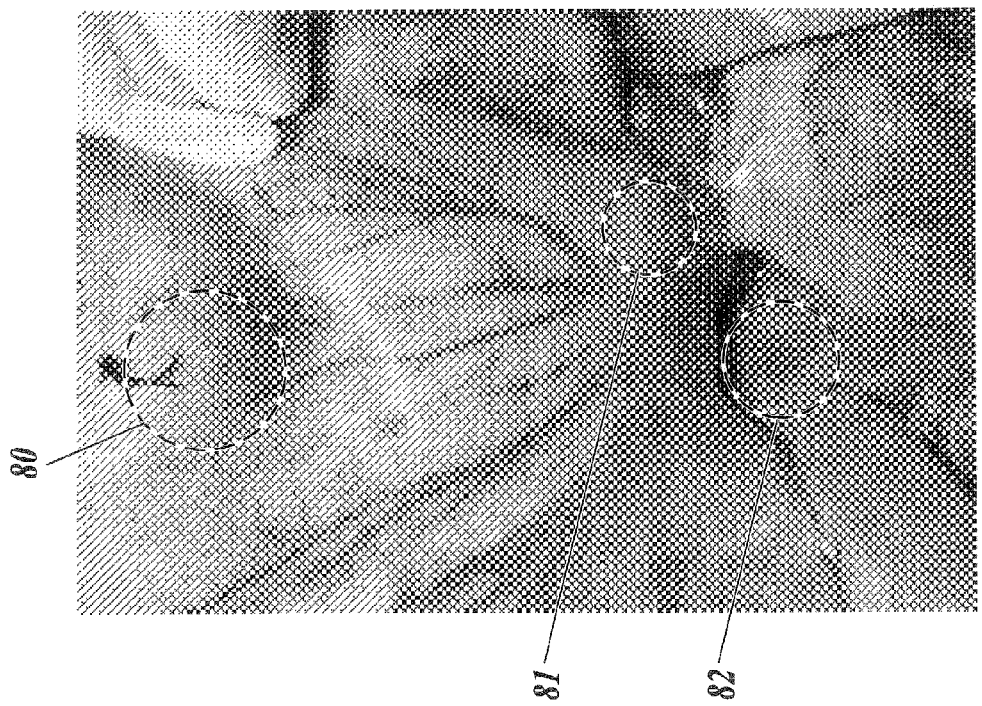

3 min.

10 min.

30 min.

60 min.

AFFERENT LYMPH VESSEL

3min.

10min.

30min.

60min.

SENTINEL LYMPH NODE

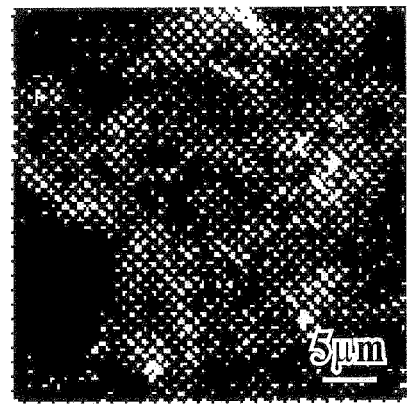
FIG.15A   0min.
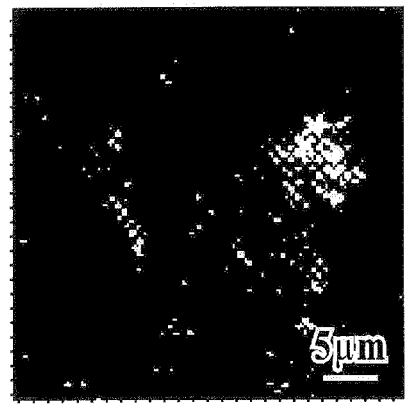
FIG.15B   30min.
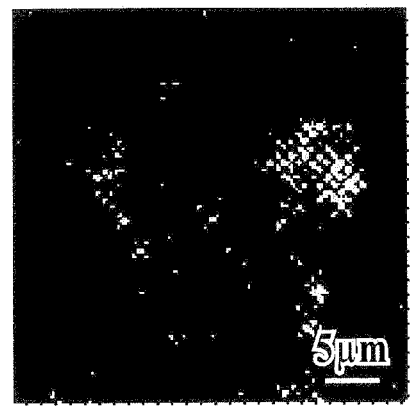
FIG.15C   60min.

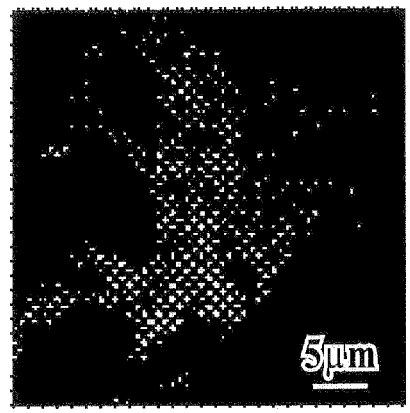
FIG.16A  0min.
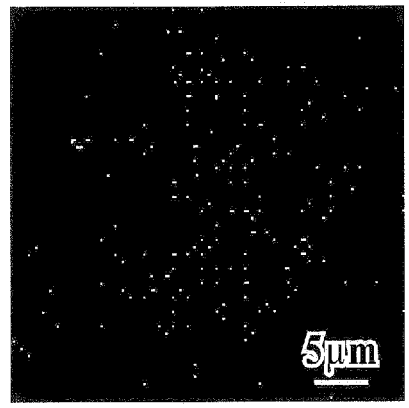
FIG.16B  30min.
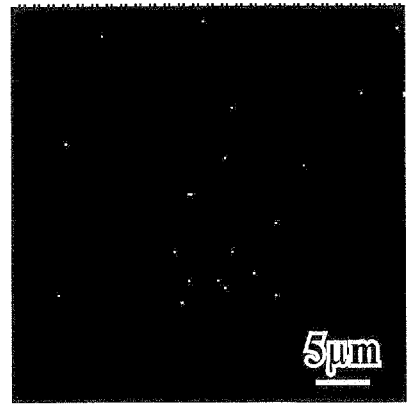
FIG.16C  60min.

FIG.23

| ANALYSIS REGION | FLUORESCENCE INTENSITY(±SEM) [$/\mu m^2$] | FLUORESCENCE INTENSITY RELATIVE VALUE (when F is taken as 1) | NUMBER OF SAMPLES |
|---|---|---|---|
| A | 5633.6 (±294.9) | 181.6 | n=10 |
| B | 3976.3 (±340.0) | 128.1 | n=10 |
| C | 633.8 (±35.5) | 20.4 | n=10 |
| D | 299.1 (±24.4) | 9.6 | n=10 |
| E | 257.6 (±36.6) | 8.3 | n=10 |
| F | 31.0 (±4.44) | 1 | n=10 |

HEATOXYLIN/EOSIN STAINING

IMMUNOSTAINING (Anti-CD3)

FIG.28

| | BODY WEIGHT [kg] | FLUORESCENCE OF INJECTED PORTION | FLUORESCENCE OF LYMPH VESSEL | NUMBER OF SLN | TIME UNTIL SLN IS DETECTED [min.] |
|---|---|---|---|---|---|
| 1 | 20 | DETECTED | DETECTED | 1 | 10 |
| 2 | 22.5 | DETECTED | DETECTED | 1 | 5 |
| 3 | 25 | DETECTED | DETECTED | 2 | IMMEDIATELY AFTER LOCAL INJECTION |
| 4 | 36.5 | DETECTED | DETECTED | 2 | IMMEDIATELY AFTER LOCAL INJECTION |
| 5 | 32 | DETECTED | DETECTED | 2 | 5 |
| 6 | 24 | DETECTED | DETECTED | 1 | 10 |

METHOD FOR DETECTING AFFERENT LYMPH VESSEL INFLOW REGIONS AND METHOD FOR IDENTIFYING SPECIFIC CELLS

CROSS REFERENCE TO RELATED APPLICATIONS

This is a 371 of PCT/JP2010/054083 filed Mar. 11, 2010, which in turn claimed the priority of Japanese Patent Application No. 2009-152781 filed Jun. 26, 2009, both both applications are incorporated by reference herein.

TECHNICAL FIELD

The present invention relates to a method for detecting afferent lymph vessel inflow regions and a method for identifying specific cells.

BACKGROUND ART

Heretofore, in an excision surgery of a cancer, in many cases, not only a lesion part but also a lymph node to which metastasis of the cancer is suspected has been excised. In recent years, a sentinel lymph node biopsy has been performed in order to minimize the excision of the lymph node.

The sentinel lymph node (SLN) is defined as a lymph node that first receives lymph flows from the respective internal organs. In the cancer surgery, such a sentinel lymph node theory is widely accepted that a radical lymph node dissection is unnecessary unless metastasis of the cancer to the sentinel lymph node is present. The sentinel lymph node biopsy makes it possible to reduce a wasteful surgical invasion, and contributes to establishment of order-made medical care in which a surgical method is finely selected in response to patient's symptoms.

In the event of performing the sentinel lymph node biopsy, it is important to enhance a detection sensitivity for a true sentinel lymph node during the surgery, and to enhance diagnosis accuracy as to whether or not the metastasis of the cancer is present in an inside of such an extirpated sentinel lymph node.

At present, materials clinically used as tracers which identify the sentinel lymph node during the surgery are coloring matter (Patent Blue, India ink and the like) and a radio isotope (RI) colloid ($^{99m}$Tc and the like); however, both of them also have many shortcomings. For example, in the case of the coloring matter, there are problems, which are: (1) in the case where dirt of anthracosis or the like is nonspecifically present in a lymph node in a living body, it becomes impossible to make evaluation as to whether or not the lymph node concerned is the sentinel lymph node; (2) an area from which the lymph node is to be dissected is contaminated, resulting in disturbance to the surgery; (3) the patient has allergy (anaphylactic reaction) to the coloring matter; and the like. Meanwhile, in the case of the RI colloid, there are such problems, which are: (1) a particle diameter of the colloid is several hundred nanometers to several ten micrometers, which is larger in comparison with those of the coloring matter (with several nanometers) and quantum dots (with several ten nanometers), and the colloid is poor in shifting to a lymphatic system, and accordingly, such a lymph flow cannot be observed in real time; (2) since resolution is low, there is an apprehension that the sentinel lymph node may escape detection in the case where the sentinel lymph node is located in the vicinity of a part into which the colloid is to be locally injected (shine-through phenomenon); (3) the RI colloid is regulated with regard to use thereof, and it is difficult to expand adaptable facilities thereof; and the like.

Moreover, in comparison with a cancer of a region having a relatively simple lymph flow, such as a breast cancer and a skin cancer, in a digestive system cancer in which the lymph flow is multi-directional and complicated, it is difficult to observe the lymph flow in real time, and accordingly, application of such a sentinel lymph node biopsy method is delayed.

For the above-described reasons, development of a new tracer excellent in detection sensitivity is expected, and there is proposed a method for detecting the sentinel lymph node, which uses fluorescent coloring matter (refer to Patent Document 1 and Patent Document 2). In particular, it is considered to be possible that quantum dots (Ws) can be such a tracer for the sentinel lymph node, which has an excellent detection sensitivity It is the largest object of the sentinel lymph node biopsy to diagnose whether or not metastatic cancer cells are present in the sentinel lymph node during the surgery. At present, the diagnosis as to whether or not the cancer metastasis to the sentinel lymph node is present is performed by a microscope after an extirpated tissue is sliced, and is stained by hematoxylin-eosin staining or the like. However, since only a tiny part of the extirpated lymph node tissue just can be observed, there is a risk that minute metastasis may escape detection. For example, in the case of a lymph node with a diameter of approximately 5 mm, even if one to three cross sections thereof are inspected, these cross sections are no more than 0.01% of the whole thereof.

In order to enhance capability of diagnosing whether or not the cancer is present, there are attempted: (1) a multiple staining method in which several types of immunostaining are combined with one another; (2) a technique for detecting the cancer cells in the inside of the tissue by extracting RNA from the whole of the lymph node tissue and performing a reverse transcriptase-polymerase chain reaction (RT-PCR) therefor; and the like. However, in the multiple staining method, as in the usual staining method, there is an apprehension that the metastasis cells may escape detection at a stage of creating a tissue slide. Moreover, the RT-PCP method has such shortcomings that the inspection is cumbersome and requires a time though the detection capability for the cancer cells is high, and the RT-PCR method concerned is not suitable for rapid diagnosis during the surgery, that only information in which the whole of the tissue is averaged is obtained, that it becomes impossible to make a pathological sample since it is necessary to inspect the whole of the tissue in order to surely find the minute metastasis, and the like.

Hence, in the pathological diagnosis in the sentinel lymph node biopsy, it is considered to be necessary to develop a technique for specifying the cancer metastasis region in the inside of the sentinel lymph node with high sensitivity and high accuracy.

In Non-Patent Document 1, there is reported a state where a melanoma tumor of the auricle of a mouse is metastasized to a regional lymph node. In accordance with this, the lymph node metastasis of the cancer occurs from the vicinity of an inflow region of an afferent lymph vessel.

PRIOR ART DOCUMENTS

Patent Documents

Patent Document 1: Japanese Patent Laid-Open Publication No. 2006-14868

Patent Document 2: Japanese Patent Laid-Open Publication No. 2004-269439

Non-Patent Document

Non-Patent Document 1: T. Hoshida, and eight others, "Imaging Steps of Lymphatic Metastasis Reveals That Vascular Endothelial Growth Factor-C Increases Metastasis by Increasing Delivery of Cancer Cells to Lymph Nodes: Therapeutic Implications", Cancer Research 2006, (U.S.), Waverly Press, Aug. 15, 2006, Vol. 66, No. 16, pp. 8065-8075

DISCLOSURE OF THE INVENTION

Problem to be Solved by the Invention

However, in the conventional technologies, even in the case of using the quantum dots as the tracer for the sentinel lymph node, the evaluation for the extirpated sentinel lymph node has remained only in a qualitative observation as to whether or not the tissue thereof shines. This is considered to result from that accuracy of a fluorescence measurement technology is low.

The present invention has been made in consideration of the problems inherent in the above-described conventional technologies. It is an object of the present invention to accurately detect a region where the metastasis cancer cells can be present in the inside of the sentinel lymph node.

Means for Solving the Problems

In order to solve the aforementioned problems, the invention according to claim 1 is a method for detecting afferent lymph vessel inflow regions, the method comprising:
measuring fluorescence intensity for each of a plurality of regions in an already extirpated sentinel lymph node into which quantum dots are injected; and
detecting one or a plurality of regions as the afferent lymph vessel inflow regions in order from one with highest fluorescence intensity among the plurality of regions for which the measuring is performed.

The invention according to claim 2 is the method for detecting afferent lymph vessel inflow regions according to claim 1,
wherein the fluorescence intensity is measured by performing, for each of the plurality of regions in the sentinel lymph node, image analysis for an image obtained by a confocal fluorescence microscope for single molecule observation.

The invention according to claim 3 is the method for detecting afferent lymph vessel inflow regions according to either one of claims 1 and 2,
wherein the quantum dots include quantum dots to which antibodies specific to specific cells are bonded, and
the specific cells are identified based on fluorescence in the sentinel lymph node.

The invention according to claim 4 is the method for detecting afferent lymph vessel inflow regions according to claim 3,
wherein the specific cells are T-lymphocytes.

The invention according to claim 5 is the method for detecting afferent lymph vessel inflow regions according to claim 3,
wherein the specific cells are cancer cells.

The invention according to claim 6 is a method for identifying specific cells, the method comprising:
measuring fluorescence intensity for each of a plurality of regions in an already extirpated sentinel lymph node into which quantum dots are injected, the quantum dots including quantum dots to which antibodies specific to specific cells are bonded;
detecting one or a plurality of regions as afferent lymph vessel inflow regions in order from one with highest fluorescence intensity among the plurality of regions for which the measuring is performed; and
identifying the specific cells based on fluorescence of the detected afferent lymph vessel inflow regions.

Effects of the Invention

In accordance with the invention according to claim 1, the regions in the sentinel lymph node, in each of which the fluorescence intensity is high, are detected as the afferent lymph vessel inflow regions, and accordingly, the regions in the sentinel lymph node, where it is possible that the metastasis cancer cells can be present, can be detected accurately.

In accordance with the invention according to claim 2, the image acquired by the confocal fluorescence microscope for the single molecule observation is subjected to the image analysis, whereby the fluorescence intensity can be accurately measured for each of the plural regions.

In accordance with the invention according to claim 3, detection accuracy for the specific cells can be enhanced.

In accordance with the invention according to claim 4, detection accuracy for the T-lymphocytes can be enhanced.

In accordance with the invention according to claim 5, detection accuracy for the cancer cells can be enhanced.

In accordance with the invention according to claim 6, the regions where it is possible that metastasis cancer cells can be present in the sentinel lymph node can be detected accurately, and in addition, the detection accuracy for the specific cells can be enhanced.

BRIEF DESCRIPTION OF THE DRAWINGS

FIG. 7A is an imaged image of a lesser curvature-side posterior wall of a gastric corpus.

FIG. 7B is a fluorescence image obtained by imaging the lesser curvature-side posterior wall of the gastric corpus by the endoscope-type fluorescence measurement device and analyzing the lesser curvature-side posterior wall concerned by the image analysis device.

FIG. 15A is a fluorescence image immediately after (zero minute) an excitation laser beam is irradiated onto the sentinel lymph node.

FIG. 15B is a fluorescence image after the excitation laser beam is irradiated onto the sentinel lymph node for 30 minutes.

FIG. 15C is a fluorescence image after the excitation laser beam is irradiated onto the sentinel lymph node for 60 minutes.

FIG. 16A is a fluorescence image immediately after (zero minute) the excitation laser beam is irradiated onto the lymph node other than the sentinel lymph node.

FIG. 16B is a fluorescence image after the excitation laser beam is irradiated onto the lymph node other than the sentinel lymph node for 30 minutes.

FIG. 16C is a fluorescence image after the excitation laser beam is irradiated onto the lymph node other than the sentinel lymph node for 60 minutes.

FIG. 23 is results of quantitative analyses of fluorescence intensities in the analysis regions A to F.

FIG. 28 is detection results of the sentinel lymph nodes.

BEST MODE FOR CARRYING OUT THE INVENTION

[Device Configuration]

A description is made below of embodiments of the present invention with reference to the drawings.

First, a description is made of a configuration of devices.

Figure 1:
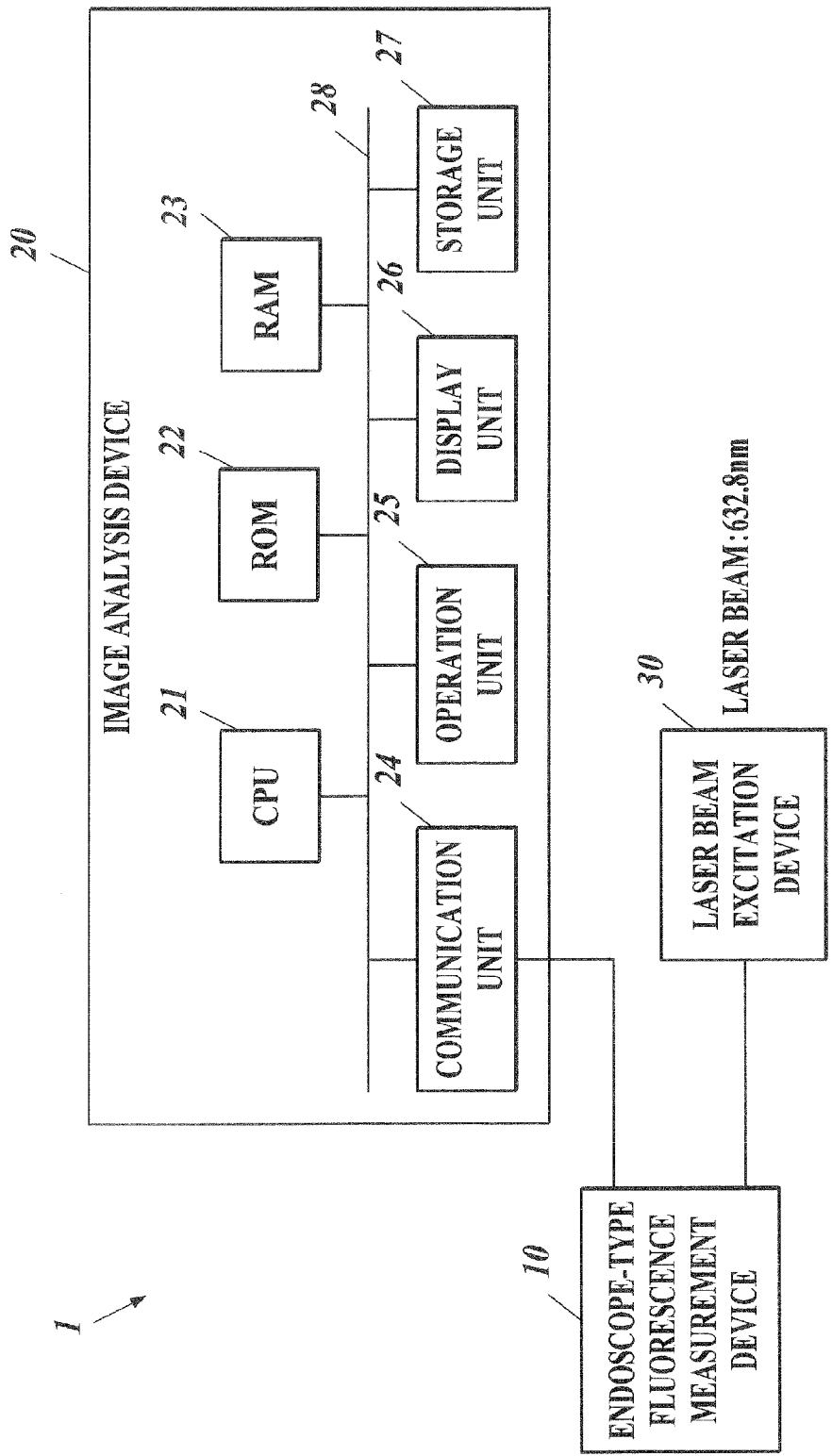
FIG. 1 is a configuration view of a fluorescence measurement system.

FIG. 1 shows a configuration of a fluorescence measurement system 1. As shown in FIG. 1, the fluorescence measurement system 1 includes: an endoscope-type fluorescence measurement device 10; an image analysis device 20; and a laser beam excitation device 30. The fluorescence measurement system 1 is a system that performs fluorescence analysis in a surgical field during surgery, and is used in the event of specifying a position of a sentinel lymph node from a living body into which quantum dots are injected as a tracer.

The quantum dots are clusters of a semiconductor with a diameter of 15 to 20 nanometers (nm), and are particles having characteristics to emit various types of fluorescence in response to a particle diameter thereof. Each of the quantum dots is composed of: a core of cadmium/selenium, which is a center thereof; and a shell, a polymer coating and the like, which cover the core. In the case of using the quantum dots as the tracer for the sentinel lymph node, there are features as below:

(1) the quantum dots have intense fluorescence intensity, and are less likely to discolored, and accordingly, enable long-time observation;
(2) in the quantum dots, there are particles with a variety of emission wavelengths, and in the case of using fluorescent particles with a wavelength longer than the visible range, the quantum dots do not contaminate the surgical field macroscopically;
(3) the quantum dots have intense fluorescence intensity, and are capable of identifying a direction of a lymph flow in real time;
(4) the particles with the variety of emission wavelengths can be detected by excitation light with the same wavelength, and it is possible to identify the particles by the emission wavelengths;
(5) there are hardly such regulations as in the event of using RI;
(6) the number of particles and the fluorescence intensity have a proportional relationship therebetween, and it is possible to quantitate the fluorescence intensity; and
(7) even at a stage where a pathological tissue section is created, the fluorescence is not deactivated, and the pathological tissue section concerned is applicable to a pathological evaluation.

Figure 2:
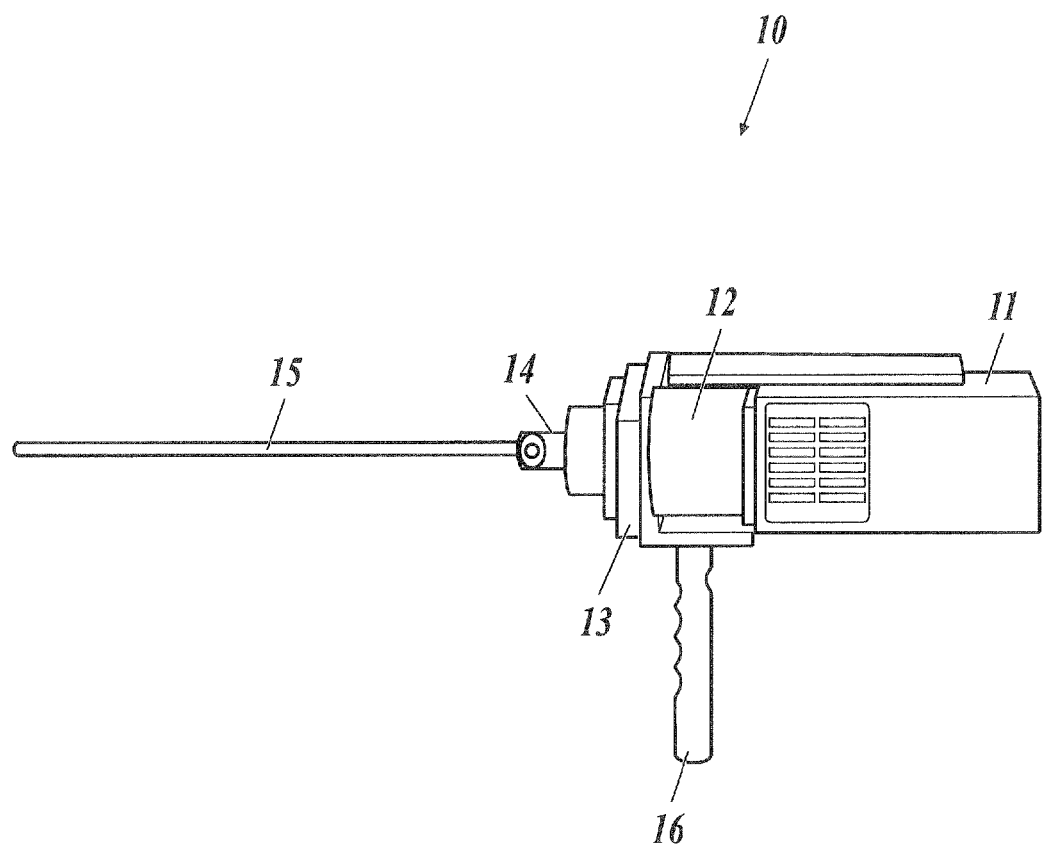
FIG. 2 is an exterior appearance configuration view of an endoscope-type fluorescence measurement device.

The endoscope-type fluorescence measurement device 10 is a high-sensitivity fluorescence measurement device for an endoscopic surgery. FIG. 2 shows an exterior configuration of the endoscope-type fluorescence measurement device 10. The endoscope-type fluorescence measurement device 10 is composed by including an EMCCD camera 11, a lens 12, a fluorescence filter 13, a light guide 14, an endoscope unit 15, a handle 16 and the like.

The endoscope unit 15 is a functional unit that irradiates excitation light, which is emitted from the laser light excitation device 30, onto a living body, and in addition, receives fluorescence from the living body. The EMCCD camera 11 is a high-sensitivity CCD camera for the endoscopic surgery, receives the fluorescence guided through the endoscope unit 15, the fluorescence filter 13 and the lens 12, and outputs image data to the image analysis device 20.

As shown in FIG. 1, the image analysis device 20 is composed by including a central processing unit (CPU) 21, a read only memory (ROM) 22, a random access memory (RAM) 23, a communication unit 24, an operation unit 25, a display unit 26, a storage unit 27 and the like, and the respective units are connected to one another by a bus 28.

The CPU 21 reads out a variety of processing programs stored in the ROM 22, expands the programs concerned in a work area formed in the RAM 23, and controls the respective units of the image analysis device 20 in accordance with the programs concerned.

The ROM 22 stores a system program to be executed by the CPU 21, stores a variety of programs for performing various pieces of processing, and stores data and the like, which are necessary to execute these programs.

In the various pieces of processing to be executed and controlled by the CPU 21, the RAM 23 temporarily stores the variety of processing programs read out from the ROM 22, input or output data, parameters and the like.

The communication unit 24 receives the image data of the fluorescence image from the endoscope-type fluorescence measurement device 10.

The operation unit 25 is composed by including a keyboard provided with cursor keys, character input keys, a variety of function keys and the like, and including a pointing device such as a mouse, and outputs, to the CPU 21, instruction signals inputted by key operations to the keyboard and mouse operations.

The display unit 26 is composed of a monitor such as a liquid crystal display (LCD), and displays an observation target image, an operation screen and the like in accordance with instructions of display signals to be inputted from the CPU 21.

The storage unit 27 is composed of a hard disk, a nonvolatile semiconductor memory and the like, and stores a variety of data. For example, the storage unit 27 stores a file (AVI file) of the image data received from the endoscope-type fluorescence measurement device 10, and the like.

The CPU 21 allows the display unit 26 to display the observation target image based on the image data of the fluorescence image, which is acquired by the endoscope-type fluorescence measurement device 10, and performs image analysis for the image data to calculate fluorescence intensity thereof.

The laser beam excitation device 30 is a device that emits an excitation laser beam (632.8 nm) to be irradiated onto the living body.

Figure 3:
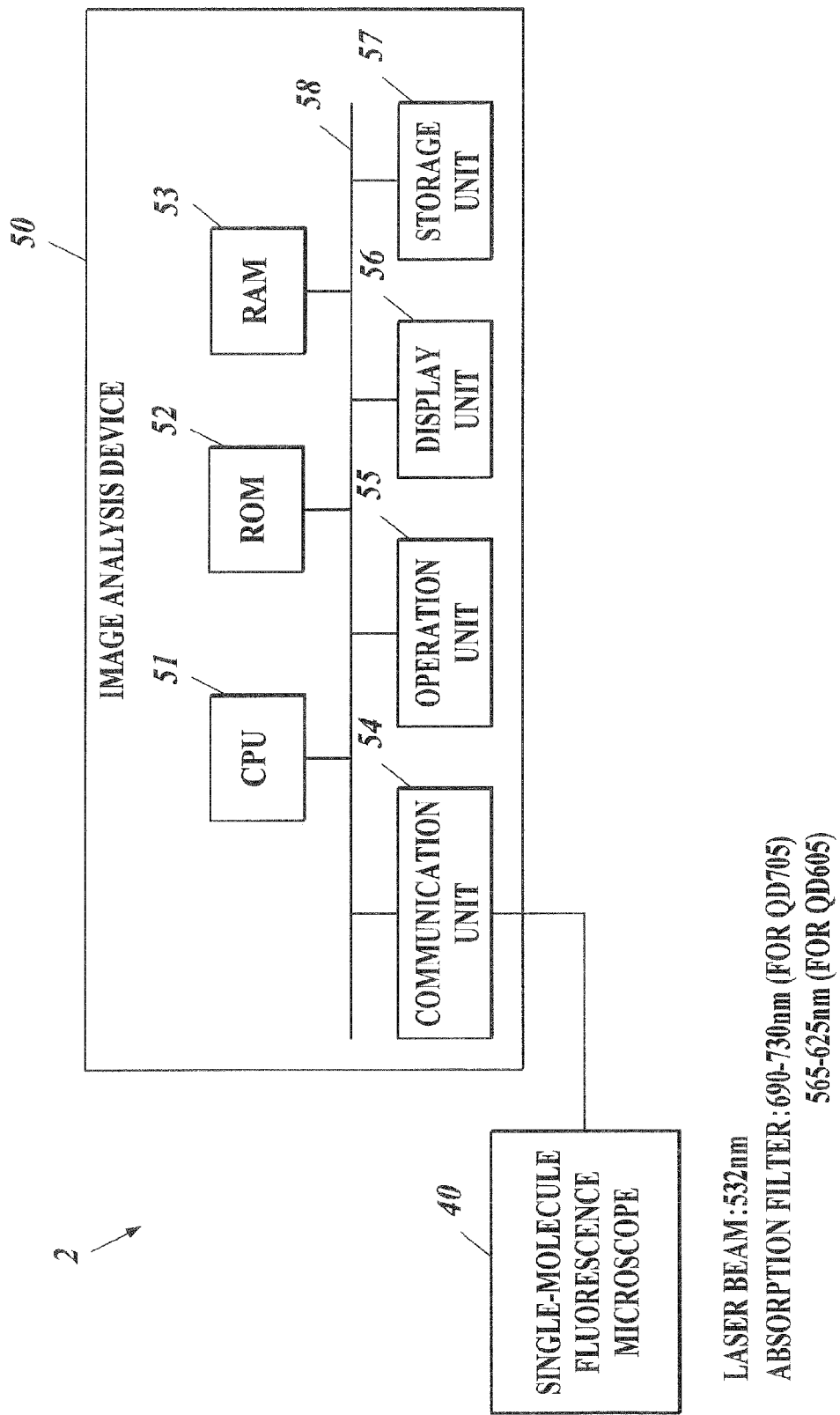
FIG. 3 is a configuration view of a microscope system.

FIG. 3 shows a configuration of a microscope system 2. As shown in FIG. 3, the microscope system 2 includes a single-molecule fluorescence microscope 40 and an image analysis device 50. The microscope system 2 is a system that performs the fluorescence analysis more precisely for a tissue extirpated from the living body, and the microscope system 2 is used in the event of analyzing a structure of an inside of the sentinel lymph node.

The single-molecule fluorescence microscope 40 is a confocal fluorescence microscope for single molecule observation, and is a confocal fluorescence microscope device capable of observation in a level of a single molecule (single fluorescence molecule). The single-molecule fluorescence microscope 40 irradiates excitation laser light (532 nm) from a light source, and outputs a fluorescence image, which comes from the observation target tissue, as image data to the image analysis device 50.

As shown in FIG. 3, the image analysis device 50 includes a CPU 51, a ROM 52, a RAM 53, a communication unit 54, an operation unit 55, a display unit 55, a storage unit 57 and the like, and the respective units are connected to one another by a bus 58.

The CPU 51 reads out a variety of processing programs stored in the ROM 52, expands the programs concerned in a work area formed in the RAM 53, and controls the respective units of the image analysis device 50 in accordance with the programs concerned.

The ROM 52 stores a system program to be executed by the CPU 51, stores a variety of programs for performing various pieces of processing, and stores data and the like, which are necessary to execute these programs.

In the various pieces of processing to be executed and controlled by the CPU 51, the RAM 53 temporarily stores the variety of processing programs read out from the ROM 52, input or output data, parameters and the like.

The communication unit 54 receives the image data from the single-molecule fluorescence microscope 40.

The operation unit 55 is composed by including a keyboard provided with cursor keys, character input keys, a variety of function keys and the like, and including a pointing device such as a mouse, and outputs, to the CPU 51, instruction signals inputted by key operations to the keyboard and mouse operations.

The display unit 56 is composed of a monitor such as a liquid crystal display (LCD), and displays an observation target image, an operation screen and the like in accordance with instructions of display signals to be inputted from the CPU 51.

The storage unit 57 is composed of a hard disk, a nonvolatile semiconductor memory and the like, and stores a variety of data. For example, the storage unit 57 stores a file (AVI file) of the image data received from the single-molecule fluorescence microscope 40, and the like.

The CPU 51 allows the display unit 56 to display the observation target image based on the image data of the fluorescence image, which is acquired by the single-molecule fluorescence microscope 40, and performs image analysis for the image data to calculate fluorescence intensity thereof.

[Sentinel Lymph Node Biopsy]

Next, a description is made of a sentinel lymph node biopsy.

In the event where a surgery to excise a cancer from the living body is performed, the quantum dots are injected as the tracer for the sentinel lymph node into the vicinity of the cancer in the living body. The quantum dots flow through lymph vessels and reach the sentinel lymph node. By the fluorescence measurement system 1, the excitation light is irradiated onto the surgical field, and the sentinel lymph node is identified based on the fluorescence. Then, the sentinel lymph node is extirpated from the living body.

Here, for the sentinel lymph node extirpated in a state where the quantum dots are injected thereinto, more precise fluorescence analysis is performed by the microscope system 2. Specifically, the fluorescence intensity is measured for each of plural regions in the sentinel lymph node, and one or plural regions are detected as afferent lymph vessel inflow regions in order from one with the highest fluorescence intensity among the plural regions for which the measurement is performed. The fluorescence intensity is measured in such a manner that such an image acquired by the single-molecule fluorescence microscope 40 is subjected to the image analysis in the image analysis device 50. Note that, in the event of detecting the afferent lymph vessel inflow regions, the predetermined number of regions may be detected as the afferent lymph vessel inflow regions in order from the one with the highest fluorescence intensity among the plural regions in the sentinel lymph node, or alternatively, regions among the plural regions, in each of which the fluorescence intensity is a predetermined criteria value or more, may be detected as the afferent lymph vessel inflow regions. The present invention is used for structure analysis for the sentinel lymph node.

Tissues of the detected afferent lymph vessel inflow regions are taken, and a histopathological examination to diagnose whether or not cancer cells are present is performed. In the case where no metastasis of the cancer is present in the afferent lymph vessel inflow regions, it is not necessary to excise the lymph node any more.

[Flow of Experiment]

Figure 4:
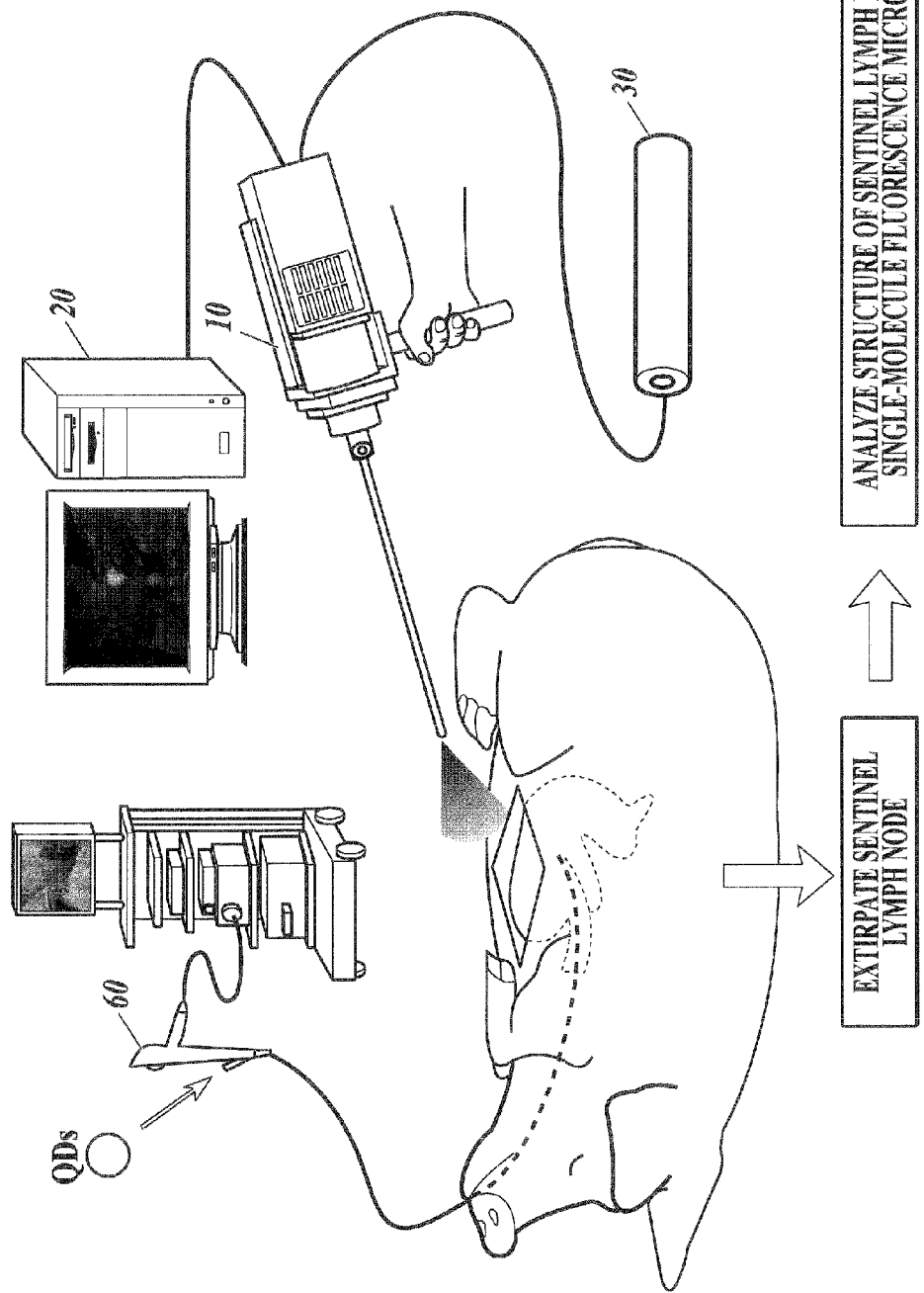
FIG. 4 is a view for explaining a flow of an experiment.

Next, a description is made of a flow of an experiment with reference to FIG. 4. FIG. 4 is an example where a pig as a representative of a large-size animal model is used as the living body, and a gastric cancer is assumed. As the pig, a male-castrated pig (average body weight: 26.7 kg) of the Landrace/Yorkshire cross bread with an age of two to three months was used.

First, general anesthesia was given to the pig, and 500 µL of quantum dots with 2 µM was locally injected into a submucosa of a lesser curvature-side posterior wall of a gastric corpus of the pig by using a local injection needle of a gastroscope 60.

As the quantum dots, Qdot (registered trademark) 705 sold by Invitrogen (registered trademark) Co., Ltd. was used. A diameter of particles of the Qdot 705 is approximately 20 nm, and an emission wavelength thereof is 702 (700 to 715) nm. The reason why the fluorescent particles with the emission wavelength of the near infrared range were selected is that a point that interference thereof with intrinsic fluorescence of the living body is a little was considered.

After the local injection of the quantum dots, fluorescence spreading of the quantum dots in a stomach and a lymphoreticular system that follows the same was observed in real time by using the endoscope-type fluorescence measurement device 10. A position of the sentinel lymph node was specified by the fluorescence, and the sentinel lymph node was extirpated by using the fluorescence as a guide.

Next, for the extirpated sentinel lymph node, the structure analysis was performed by precise fluorescence measurement using the single-molecule fluorescence microscope 40.

[Experimental Results]

<Relationship Between Quantum Dot Concentration and Fluorescence Intensity>

Figure 5:
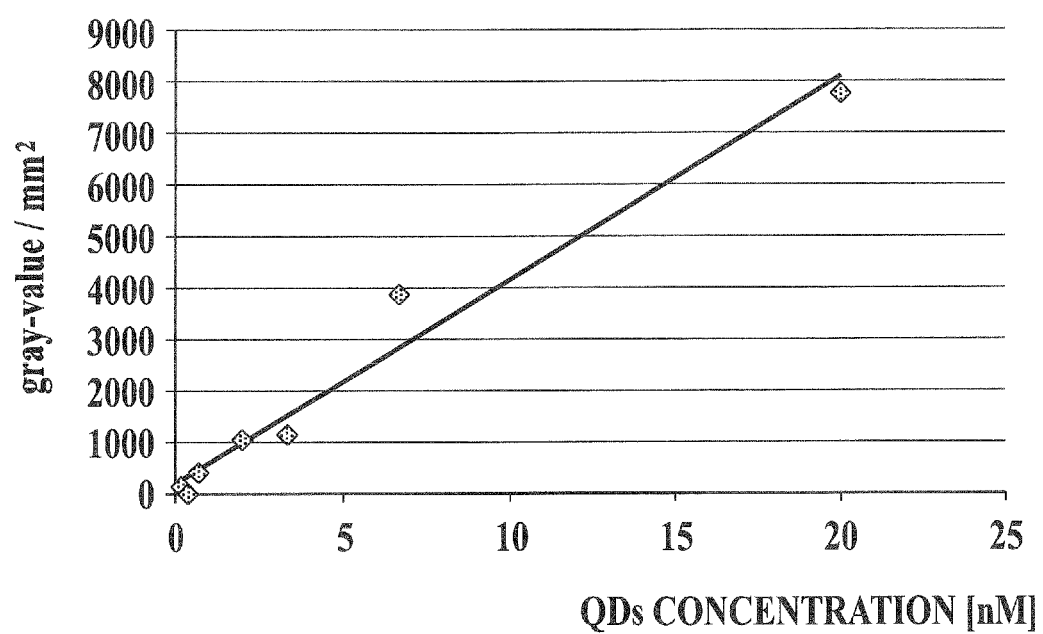
FIG. 5 is a graph showing a relationship between a quantum dot concentration and fluorescence intensity.

FIG. 5 shows a relationship between a quantum dot concentration (QDs concentration and the fluorescence intensity. A graph shown in FIG. 5 is a result obtained by injecting the quantum dots with a variety of concentrations into a gastric wall of the pig and measuring the fluorescence intensity by using the endoscope-type fluorescence measurement device 10. An axis of abscissas of the graph is the quantum dot concentration (nM), and an axis of ordinates thereof is a gray-value/mm$^2$. That is to say, in the image analysis device 20, the fluorescence intensity is calculated based on a tone of each fluorescence image acquired by the endoscope-type fluorescence measurement device 10.

It has been confirmed that the quantum dot concentration and the fluorescence intensity have a proportional relationship therebetween as shown in FIG. 5. Hence, it has been found out that it is possible to perform quantitative analysis for the fluorescence intensity by the endoscope-type fluorescence measurement device 10.

<Fluorescence Detection in Surgical Field>

Figure 6B:
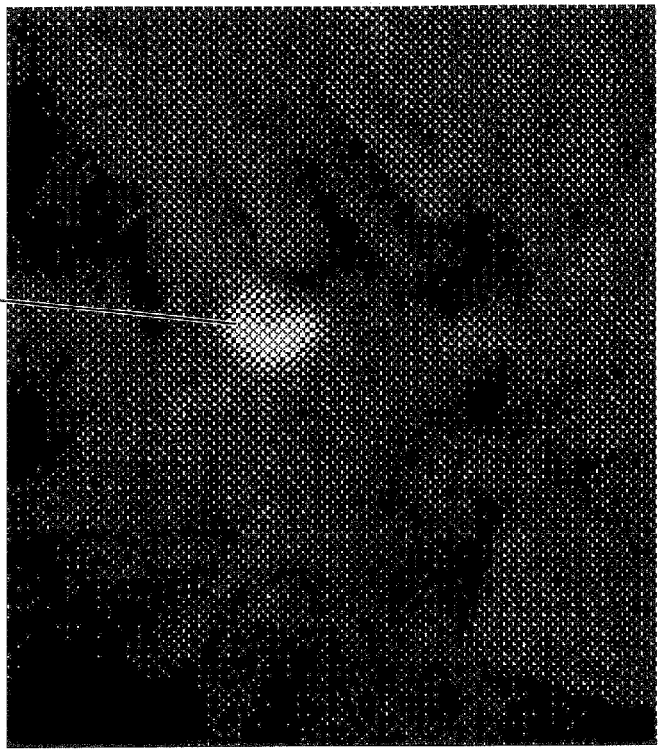
FIG. 6B is a fluorescence image obtained by analyzing, by an image analysis device, surgical field information acquired by the endoscope-type fluorescence measurement device.
Figure 6A:
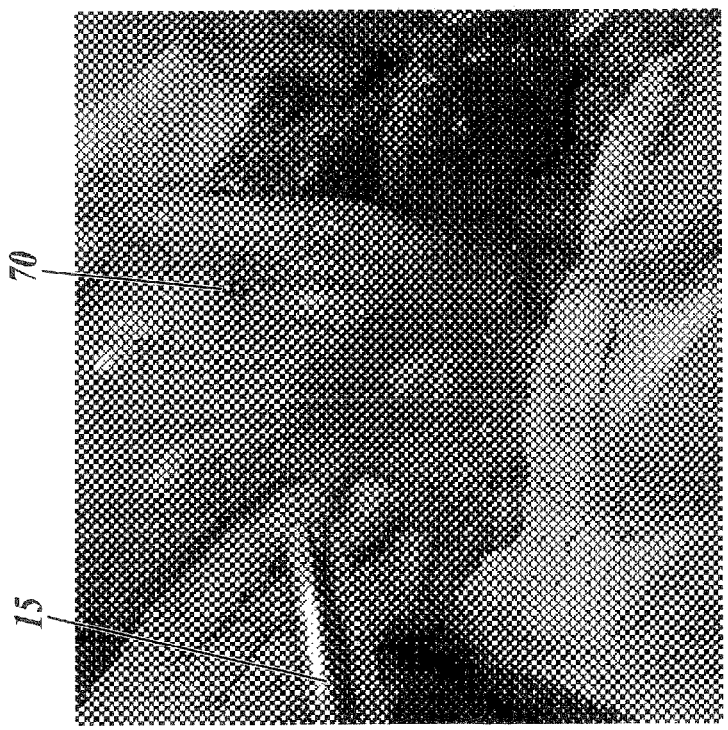
FIG. 6A is an imaged image in which a state of measurement by the endoscope-type fluorescence measurement device in a surgical field is imaged.

FIG. 6A is an imaged image in which a state of the measurement by the endoscope-type fluorescence measurement device 10 in the surgical field is imaged. The excitation light is irradiated onto an observation target region of the living body from a tip end of the endoscope unit 15 of the endoscope-type fluorescence measurement device 10. An injection portion 70 is a position into which the quantum dots were injected.

FIG. 6B is a fluorescence image obtained by analyzing, by the image analysis device 20, surgical field information acquired by the endoscope-type fluorescence measurement device 10. An injection portion 70a as a position corresponding to the injection portion 70 of the imaged image in FIG. 6A exhibits the fluorescence. That is to say, the fluorescence was detected at the position into which the quantum dots were injected.

<Observation of Inflow of Quantum Dots>

FIG. 7A is an imaged image of the lesser curvature-side posterior wall of the gastric corpus. The quantum dots injected from an injection portion 80 in an inside of the stomach flow into a sentinel lymph node 81, and do not flow into a lymph node 82 other than the sentinel lymph node.

FIG. 7B is a fluorescence image obtained by imaging the lesser curvature-side posterior wall of the gastric corpus by the endoscope-type fluorescence measurement device 10 and analyzing the lesser curvature-side posterior wall concerned by the image analysis device 20. Even in a wide viewing field, fluorescence signals were recognizable at an injection portion 80a and a portion of a sentinel lymph node 81a. Note that, with regard to a lymph node 82a other than the sentinel lymph node, the fluorescence signal was not exhibited.

<Temporal Change of Fluorescence Signal Intensity>

Figure 8A:
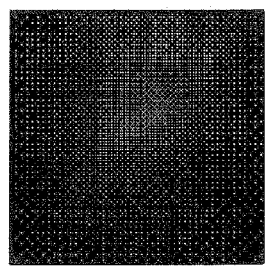
FIG. 8A is a fluorescence image of an afferent lymph vessel at a time when three minutes elapse after injection of quantum dots.
Figure 8B:
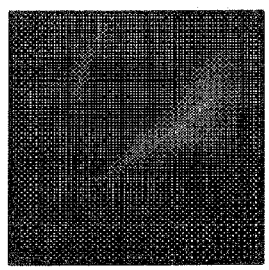
FIG. 8B is a fluorescence image of the afferent lymph vessel at a time when 10 minutes elapse after the injection of the quantum dots.
Figure 8C:
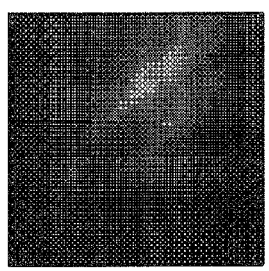
FIG. 8C is a fluorescence image of the afferent lymph vessel at a time when 30 minutes elapse after the injection of the quantum dots.
Figure 8D:
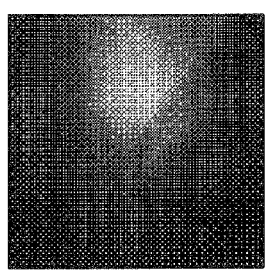
FIG. 8D is a fluorescence image of the afferent lymph vessel at a time when 60 minutes elapse after the injection of the quantum dots.
Figure 8E:
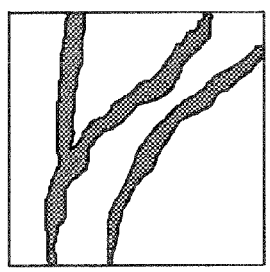
FIG. 8E is a schematic view of the afferent lymph vessel.

FIGS. 8A to 8D are fluorescence images showing chronological changes of the fluorescence signal of the afferent lymph vessel (afferent lymph vessel 83a shown in FIG. 7B), which is acquired by the endoscope-type fluorescence measurement device 10. The afferent lymph vessel is a lymph vessel at a portion where the lymph is poured into the lymph node. FIG. 8A is an image at a time when three minutes elapse after the injection of the quantum dots, FIG. 8B is an image at a time when 10 minutes elapse after the injection of the quantum dots, FIG. 8C is an image at a time when 30 minutes elapse after the injection of the quantum dots, and FIG. 8D is an image at a time when 60 minutes elapse after the injection of the quantum dots. FIG. 5E is a schematic view of the afferent lymph vessel, which corresponds to FIGS. 8A to 8D.

Figure 9A:
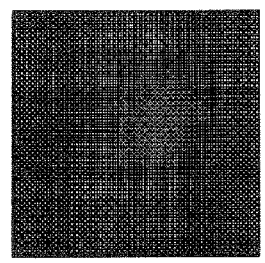
FIG. 9A is a fluorescence image of a sentinel lymph node at the time when three minutes elapse after the injection of the quantum dots.
Figure 9B:
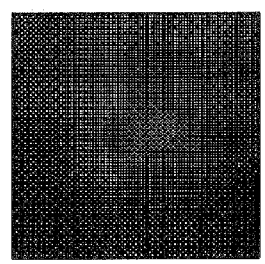
FIG. 9B is a fluorescence image of the sentinel lymph node at the time when 10 minutes elapse after the injection of the quantum dots.
Figure 9C:
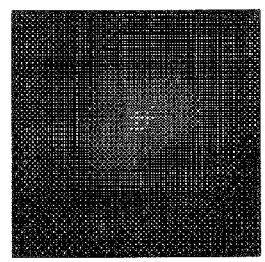
FIG. 9C is a fluorescence image of the sentinel lymph node at the time when 30 minutes elapse after the injection of the quantum dots.
Figure 9D:
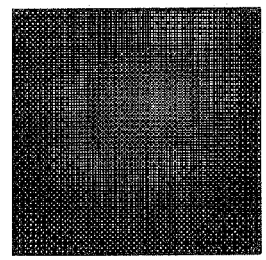
FIG. 9D is a fluorescence image of the sentinel lymph node at the time when 60 minutes elapse after the injection of the quantum dots.
Figure 9E:
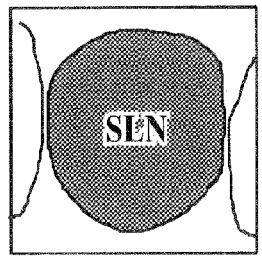
FIG. 9E is a schematic view of the sentinel lymph node.

FIGS. 9A to 9D are fluorescence views showing chronological changes of the fluorescence signal of the sentinel lymph node (sentinel lymph node 81a shown in FIG. 7B), which is acquired by the endoscope-type fluorescence measurement device 10. FIG. 9A is an image at a time when three minutes elapse after the injection of the quantum dots, FIG. 9B is an image at a time when 10 minutes elapse after the injection of the quantum dots, FIG. 9C is an image at a time when 30 minutes elapse after the injection of the quantum dots, and FIG. 9D is an image at a time when 60 minutes elapse after the injection of the quantum dots. FIG. 9E is a schematic view of the sentinel lymph node, which corresponds to FIG. 9A to FIG. 9D.

As shown in FIG. 8A to FIG. 8D, in the afferent lymph vessel, the intensity of the fluorescence signal thereof was hardly changed. Moreover, as shown in FIG. 9A to FIG. 9D, in the sentinel lymph node, the fluorescence signal thereof was intensified with time. The fluorescence signal did not leak to the peripheries of the lymph vessel and the lymph node, and the fluorescence was not recognized in the lymph node (lymph node other than the sentinel lymph node) that followed the sentinel lymph node.

Figure 10:
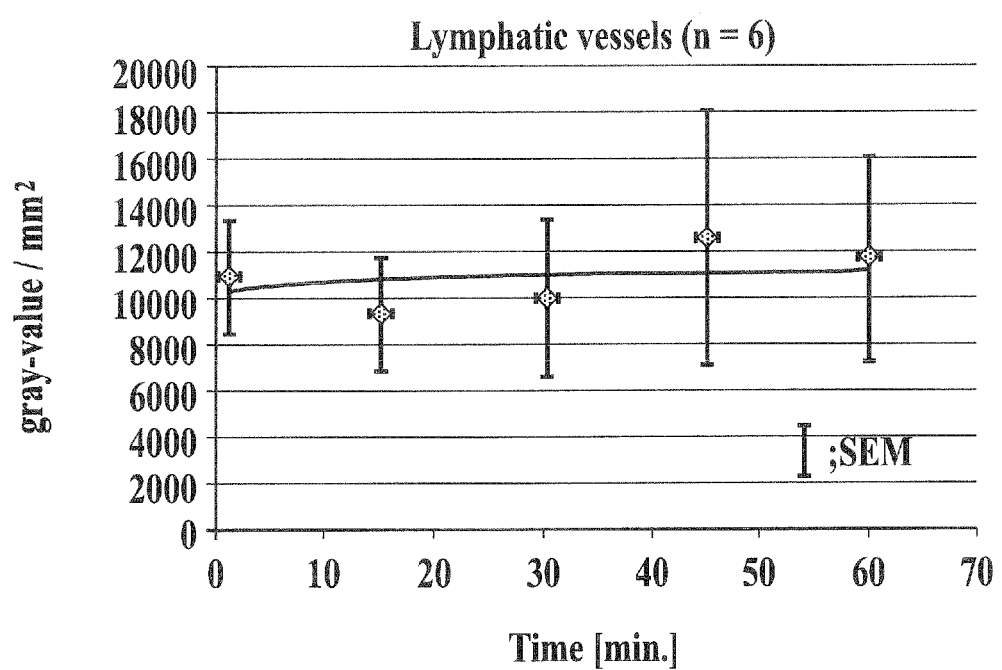
FIG. 10 is a graph in which fluorescence signal intensities in the afferent lymph vessel are quantitatively analyzed.
Figure 11:
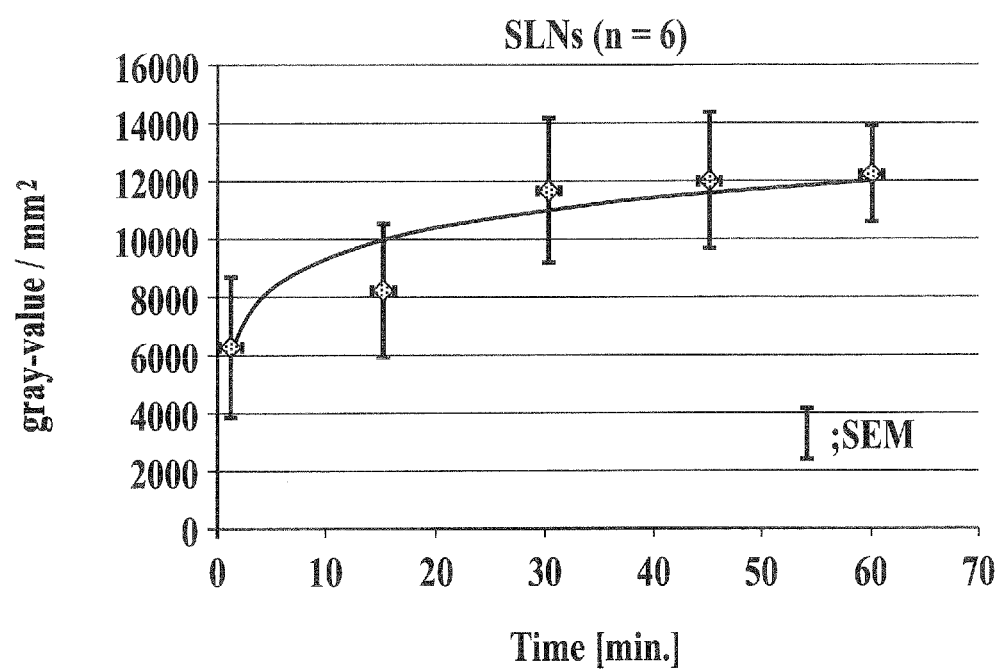
FIG. 11 is a graph in which fluorescence signal intensities in the sentinel lymph node are quantitatively analyzed.

FIG. 10 is a graph in which the fluorescence signal intensities in the afferent lymph vessel, which are acquired by the endoscope-type fluorescence measurement device 10, are quantitatively analyzed. FIG. 11 is a graph in which the fluorescence signal intensities in the sentinel lymph node, which are acquired by the endoscope-type fluorescence measurement device 10, are quantitatively analyzed. In FIG. 10 and FIG. 11, axes of abscissas are a time (minute), and axes of ordinates are gray-value/mm$^2$. In the afferent lymph vessel, data in which the fluorescence intensity was not changed with time was obtained, and in the sentinel lymph node, data in which the fluorescence intensity was increased with time was obtained.

<Observation of Fluorescence of Extirpated Lymph Node>

Figure 12A:
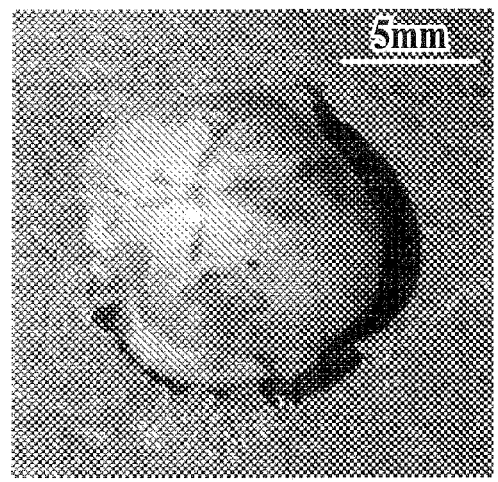
FIG. 12A is an imaged image of the sentinel lymph node.
Figure 12B:
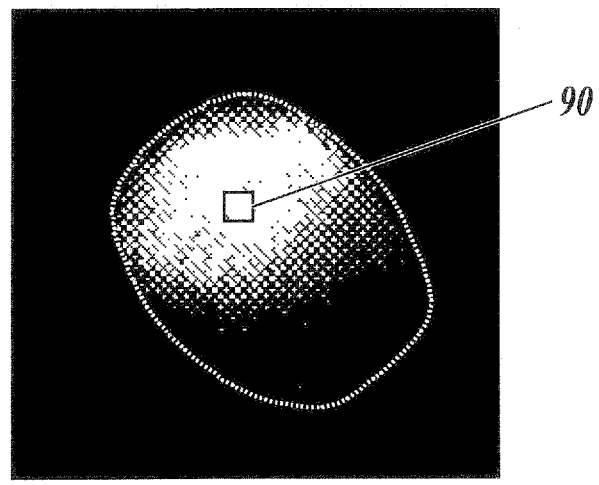
FIG. 12B is a fluorescence image of the sentinel lymph node.
Figure 12C:
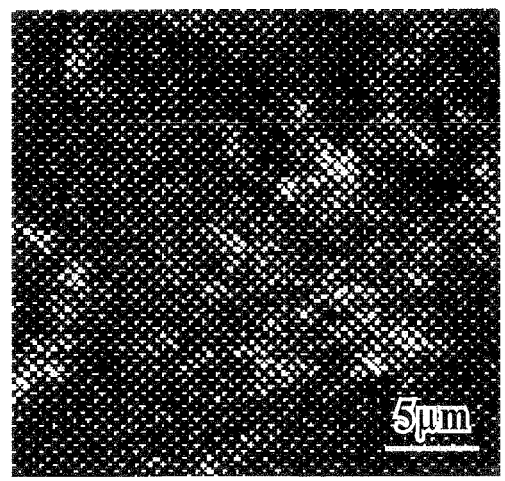
FIG. 12C is a fluorescence image obtained by imaging a part of the sentinel lymph node by a single-molecule fluorescence microscope.

FIG. 12A is an imaged image of the sentinel lymph node after being extirpated. FIG. 12B is a fluorescence image obtained by imaging this sentinel lymph node by the endoscope-type fluorescence measurement device 10. FIG. 12C is a fluorescence image after a tissue of a region 90 shown in FIG. 12B was fixed, the fluorescence image having been obtained by imaging the tissue concerned by the single-molecule fluorescence microscope 40. In the sentinel lymph node, the fluorescence was recognized even after such extirpation thereof, and in the observation in the single-molecule fluorescence microscope 40, a blinking fluorescence signal intrinsic to the quantum dots was recognized in the inside of the lymph node tissue.

Figure 13A:
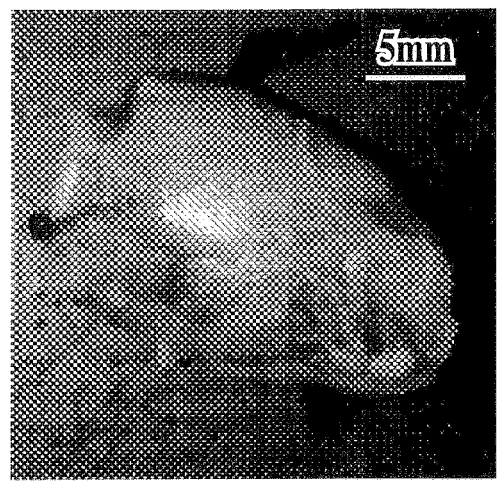
FIG. 13A is an imaged image of a lymph node other than the sentinel lymph node.
Figure 13B:
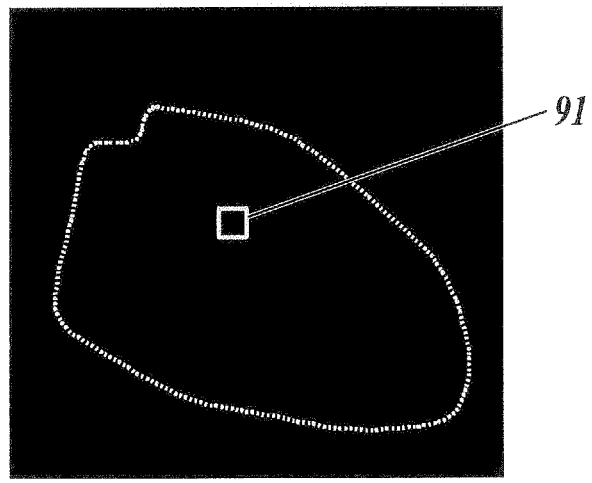
FIG. 13B is a fluorescence image of the lymph node other than the sentinel lymph node.
Figure 13C:
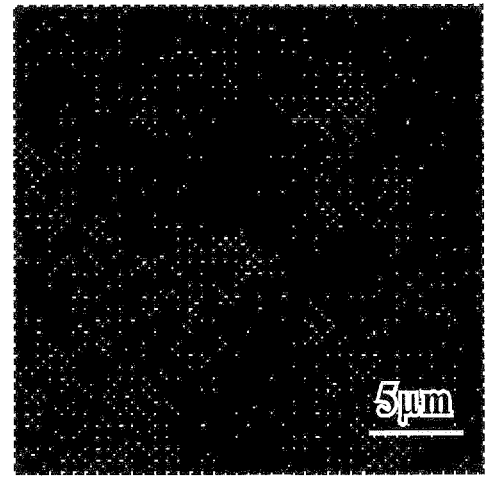
FIG. 13C is a fluorescence image obtained by imaging a part of the lymph node other than the sentinel lymph node by the single-molecule microscope.

FIG. 13A is an imaged image of the lymph node other than the sentinel lymph node after being extirpated. FIG. 13B is a fluorescence image obtained by imaging the lymph node other than the sentinel lymph node, which is shown in FIG. 13A, by the endoscope-type fluorescence measurement device 10. FIG. 13C is a fluorescence image after a tissue of a region 91 shown in FIG. 13B was fixed, the fluorescence image having been obtained by imaging the tissue concerned by the single-molecule fluorescence microscope 40. In the lymph node other than the sentinel lymph node, the fluorescence signal was not recognized in the observations by the endoscope-type fluorescence measurement device and by the single-molecule fluorescence microscope 40.

Figure 14:
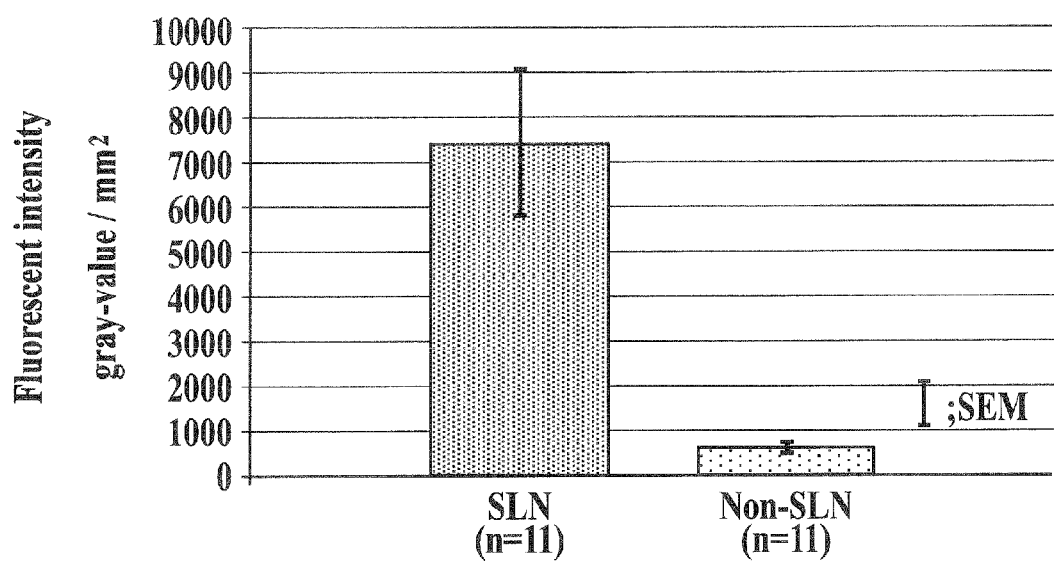
FIG. 14 is a graph showing fluorescence intensities of insides of the sentinel lymph node and the lymph node other than the sentinel lymph node.

FIG. 14 shows the fluorescence intensities (gray-value/mm$^2$) of the insides of the sentinel lymph node (SLN) and the lymph node (Non-SLN) other than the sentinel lymph node, the fluorescence intensities having been quantitatively analyzed by the endoscope-type fluorescence measurement device 10 and the image analysis device 20. The fluorescence intensity was obviously higher in the sentinel lymph node, and it has been exhibited that the quantum dots are present in the sentinel lymph node. It is considered that the fluorescence signal measured in the lymph node other than the sentinel lymph node is derived from the intrinsic fluorescence of the tissue.

<Influence of Intrinsic Fluorescence>

In the event of accurately performing the quantitative analysis for the fluorescence of the quantum dots in the tissue sample, an influence of the intrinsic fluorescence of the tissue becomes a problem. Such a near infrared range used by the inventors of the present invention is a wavelength range in which the intrinsic fluorescence of the living body is relatively small; however, in order to suppress the intrinsic fluorescence concerned as much as possible, there was examined discoloration of the intrinsic fluorescence of the tissue by an excitation laser beam (wavelength: 532 nm; irradiation surface output: 80 pW/μm$^2$) of the single-molecule fluorescence microscope 40.

FIG. 15A, FIG. 15B and FIG. 15C are fluorescence images showing the fluorescence signal at the respective points of time, which are: immediately after (zero minute) the excitation laser beam was irradiated onto the same viewing field of the sentinel lymph node by the single-molecule fluorescence microscope 40; after 30 minutes elapsed when the excitation laser beam was continuously irradiated thereonto; and after 60 minutes elapsed when the excitation laser beam was continuously irradiated thereonto.

In a similar way, FIG. 16A, FIG. 16B and FIG. 16C are fluorescence images showing the fluorescence signal at the respective points of time, which are: immediately after (zero minute) the excitation laser beam was irradiated onto the same viewing field of the lymph node other than the sentinel lymph node by the single-molecule fluorescence microscope 40; after 30 minutes elapsed when the excitation laser beam was continuously irradiated thereonto; and after 60 minutes elapsed when the excitation laser beam was continuously irradiated thereonto.

As shown in FIG. 15A to FIG. 15C and FIG. 16A to FIG. 16C, the intrinsic fluorescence of the lymph node tissue was discolored with time; however, the fluorescence signal (blinking particle signal) of the quantum dots in the inside of the sentinel lymph node tissue was not deactivated even after the excitation laser beam was irradiated for 60 minutes.

Figure 17:
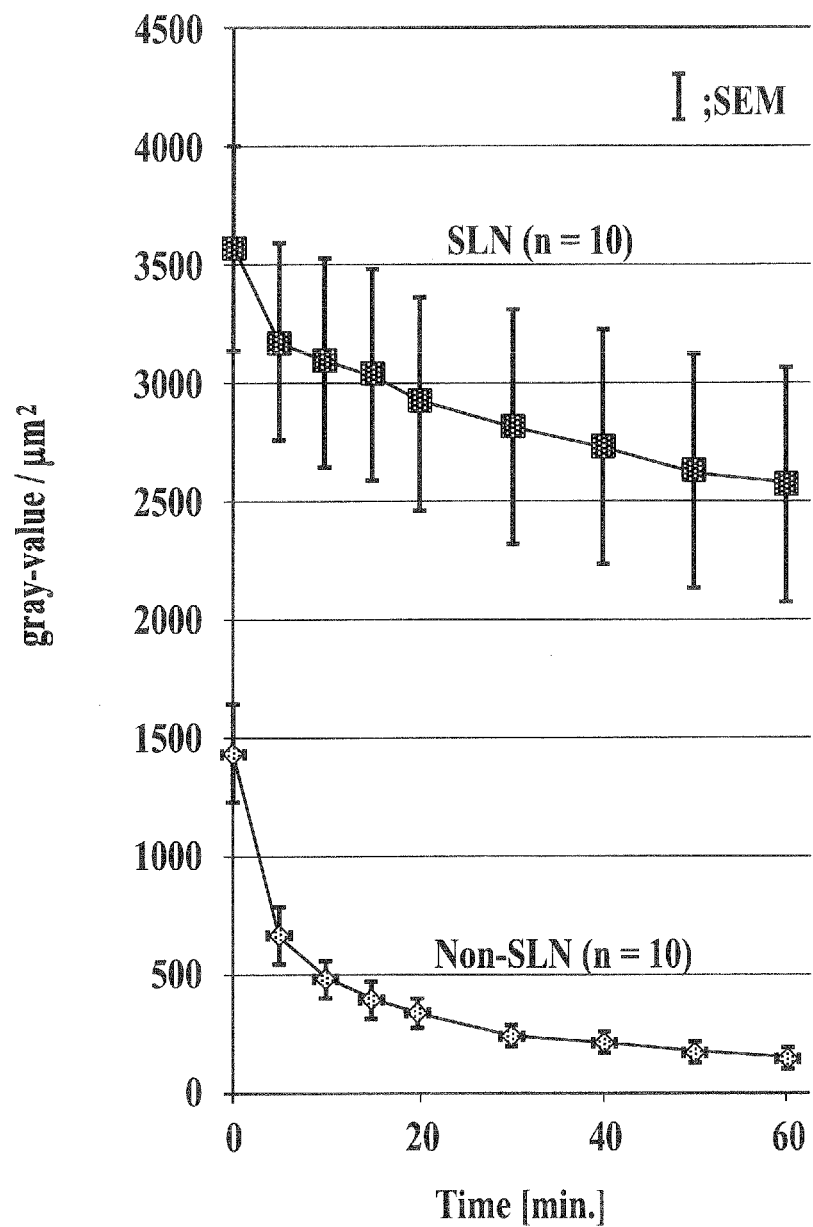
FIG. 17 is a graph showing discoloration of the fluorescence by the irradiation of the excitation laser beam in each of sample groups of the sentinel lymph node and the lymph node other than the sentinel lymph node.

FIG. 17 is a graph showing, in the quantitative evaluation, the discoloration of the fluorescence by the irradiation of the excitation laser beam of the single-molecule fluorescence microscope 40 in each of sample groups of the sentinel lymph node (SLN) and the lymph node (Non-SLN) other than the sentinel lymph node. An axis of abscissas is a time (minute), and an axis of ordinates is a gray-value/$\mu m^2$. That is to say, in the image analysis device 50, the fluorescence intensity is calculated based on a tone of each fluorescence image acquired by the single-molecule fluorescence microscope 40.

Figure 18:
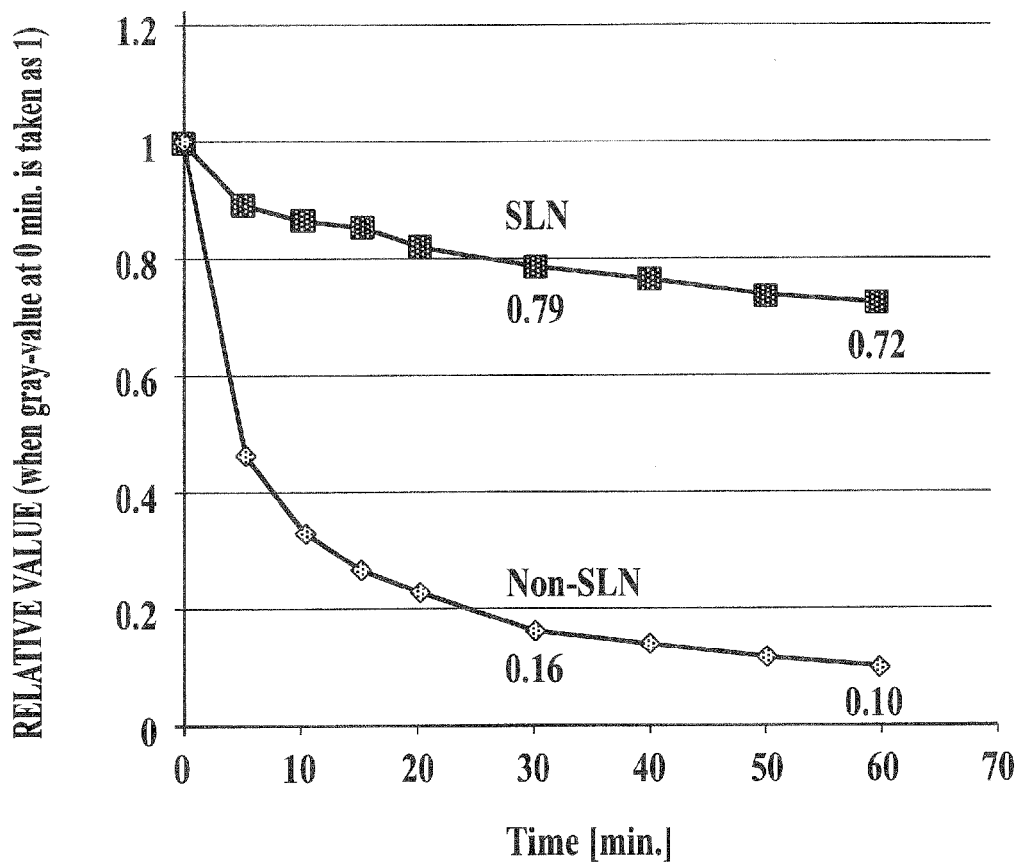
FIG. 18 is a graph expressing the graph of FIG. 17 by relative values.

FIG. 18 is a graph expressing the graph of FIG. 17 by relative values with regard to the discoloration of the fluorescence of the sentinel lymph node (SLN) and the lymph node (Non-SLN) other than the sentinel lymph node by the laser beam irradiation. For each of the sentinel lymph node and the lymph node other than the sentinel lymph node, a gray-value at zero minute is taken as 1. As shown in FIG. 18, in both of the sentinel lymph node and the lymph node other than the sentinel lymph node, results were obtained that the fluorescence was discolored by the irradiation of the excitation laser beam.

Figure 19:
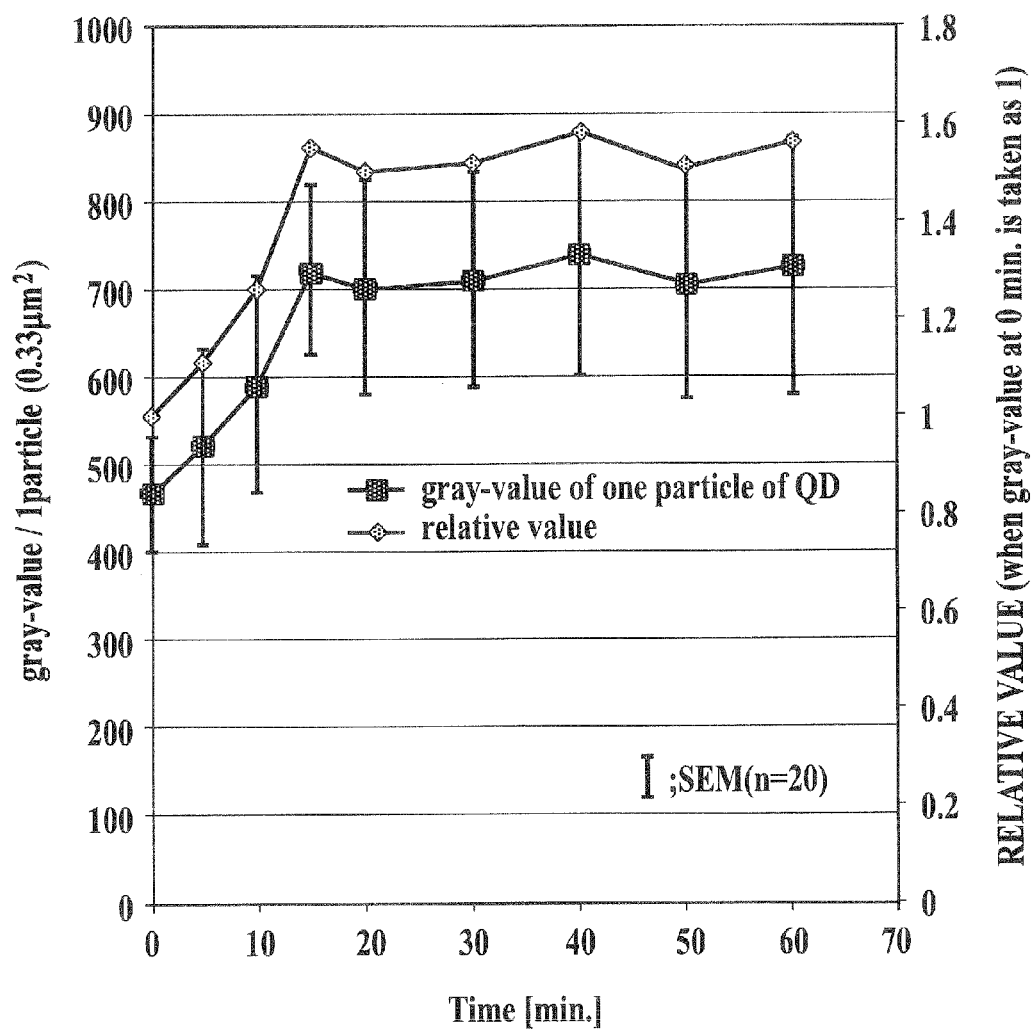
FIG. 19 is a graph showing a chronological change of fluorescence signal intensity of one particle of the quantum dot in the sample of the sentinel lymph node.

Next, while paying attention to a bright spot of one particle of the quantum dots in the sample of the sentinel lymph node, the change of the fluorescence signal intensity by the irradiation of the excitation laser beam was analyzed. FIG. 19 is a graph showing a chronological change of the fluorescence signal intensity of one particle of the quantum dots in the sample of the sentinel lymph node. FIG. 19 shows, with regard to the quantum dots of 20 as the number of samples (n=20), results (gray-values per particle, and relative values in the case where the gray-value at zero minute is taken as 1) of analyzing the fluorescence in an area with a size of 576×576 nm around the bright spot of each particle of the quantum dots. As a result, the florescence signal was increased until 15 minutes, and thereafter, was maintained until 60 minutes. From this fact, it was exhibited that the reduction of the fluorescence signal of the sample of the lymph node, which was obtained in FIG. 17 and FIG. 18, was derived from the intrinsic fluorescence of the lymph node tissue, and that the fluorescence of the quantum dots was not discolored by the irradiation of the excitation laser beam for 60 minutes.

From the results obtained above, it was exhibited that the fluorescence (intrinsic fluorescence of the tissue) of the lymph node other than the sentinel lymph node was reduced to an ignorable level (16% for 30 minutes, 10% for 60 minutes) by the irradiation of the excitation laser beam. Meanwhile, in the sentinel lymph node, it was exhibited that, while the intrinsic fluorescence of the inside thereof was reduced, the fluorescence of the quantum dots was maintained for one hour. From this data, it has been found out that, in the event of observing the tissue section by the single-molecule fluorescence microscope 40, the irradiation of the excitation laser beam for approximately 30 minutes is added, whereby a major part of the intrinsic fluorescence of the tissue is discolored, and it becomes possible to quantitatively analyze the fluorescence intensity of the quantum dots accurately.

<Heterogeneity of Quantum Dots in Inside of Sentinel Lymph Node>

In the sentinel lymph node, the fluorescence signal is heterogeneous, and this is considered to be derived from a distribution of the quantum dots in the inside of the sentinel lymph node.

Figure 20A:
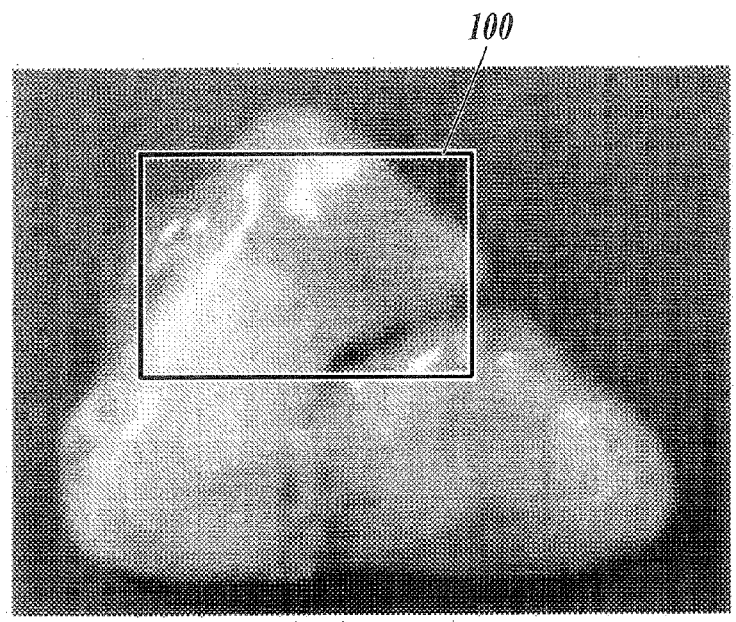
FIG. 20A is an imaged image of the sentinel lymph node.
Figure 20B:
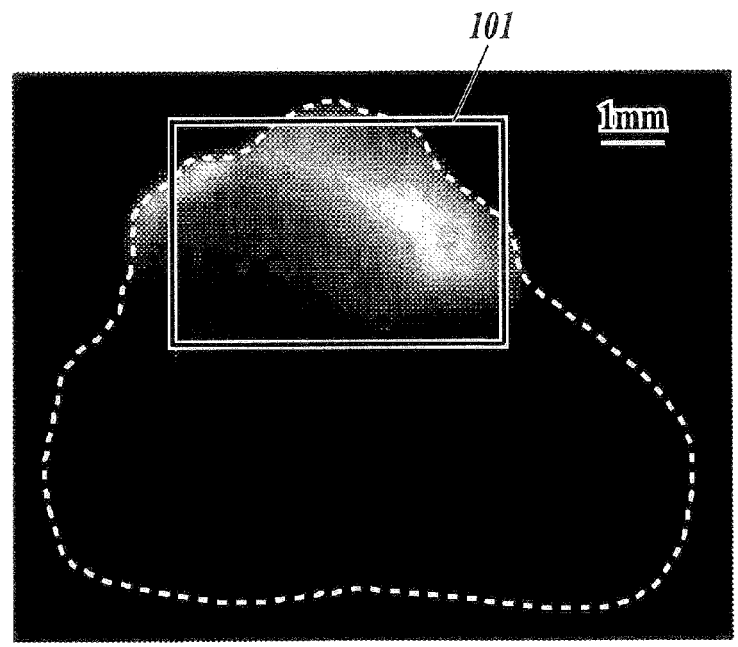
FIG. 20B is a fluorescence image of the sentinel lymph node.

FIG. 20A is an imaged image of the extirpated sentinel lymph node, and FIG. 20B is a fluorescence image of the sentinel lymph node, which is acquired by the endoscope-type fluorescence measurement device 10.

Figure 21:
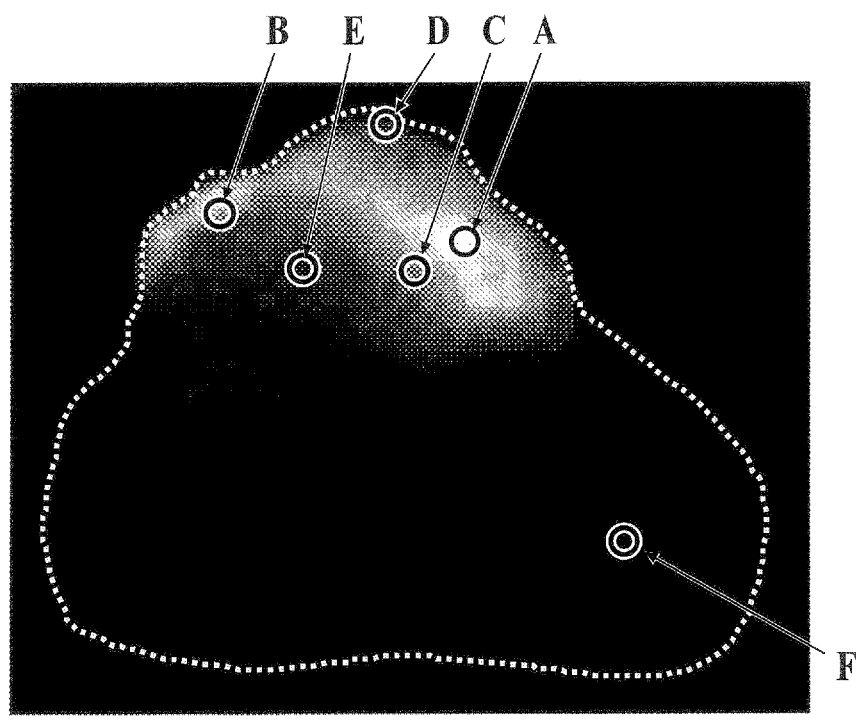
FIG. 21 is a view showing positions of analysis regions A to F in the sentinel lymph node.

The fluorescence intensity (proportional to the number of present quantum dots) in each region of the sample of the sentinel lymph node was analyzed by the single-molecule fluorescence microscope 40. FIG. 21 shows positions of analysis regions A to F in the inside of the sentinel lymph node. In order to reduce the intrinsic fluorescence of the tissue for the purpose of accurately performing the quantitative evaluation for the fluorescence, each of the analysis regions was observed after the excitation laser beam was irradiated thereonto for 30 minutes by the single-molecule fluorescence microscope 40.

Figure 22A:
FIG. 22A is a fluorescence image obtained by imaging a tissue of the analysis region A by the single-molecule fluorescence microscope.
Figure 22B:
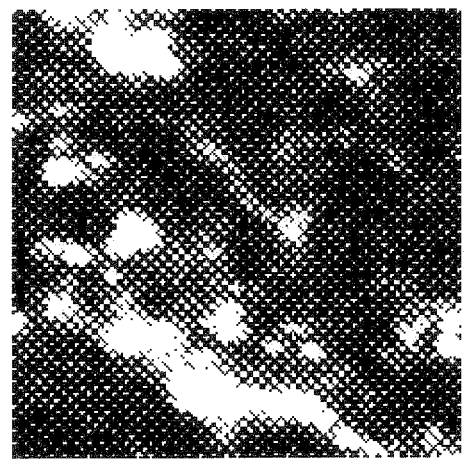
FIG. 22B is a fluorescence image obtained by imaging a tissue of the analysis region B by the single-molecule fluorescence microscope.
Figure 22C:
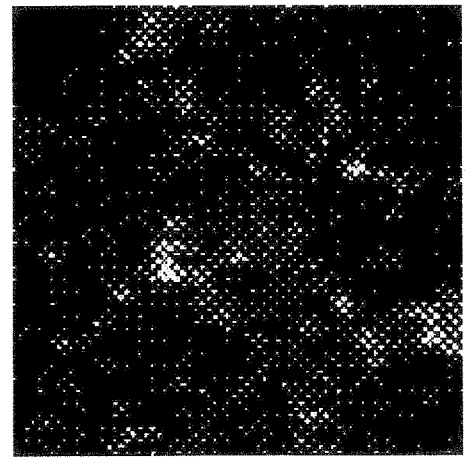
FIG. 22C is a fluorescence image obtained by imaging a tissue of the analysis region C by the single-molecule fluorescence microscope.
Figure 22D:
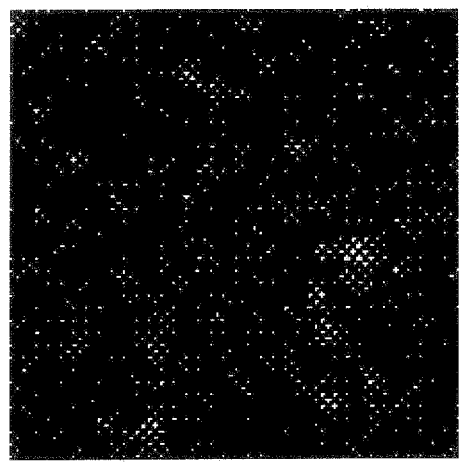
FIG. 22D is a fluorescence image obtained by imaging a tissue of the analysis region D by the single-molecule fluorescence microscope.
Figure 22E:
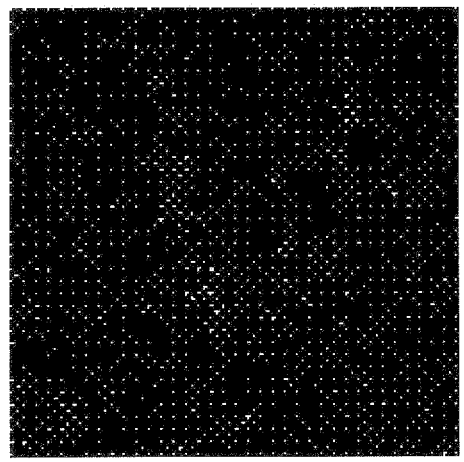
FIG. 22E is a fluorescence image obtained by imaging a tissue of the analysis region E by the single-molecule fluorescence microscope.
Figure 22F:
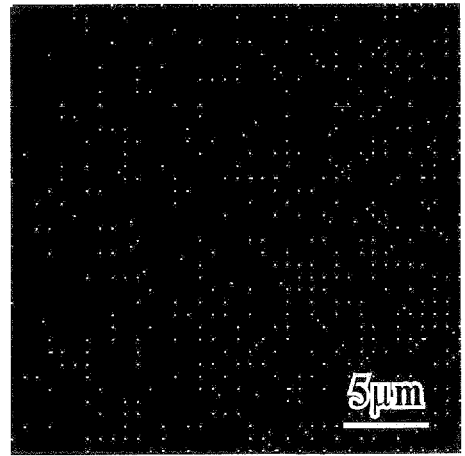
FIG. 22F is a fluorescence image obtained by imaging a tissue of the analysis region F by the single-molecule fluorescence microscope.

FIG. 22A to FIG. 22F show fluorescence images obtained by imaging the tissues of the respective analysis regions A to F by the single-molecule fluorescence microscope 40. As shown in FIG. 22A and FIG. 22B, a large number of the quantum dots was present in each of the analysis regions A and B.

FIG. 23 shows results of quantitatively analyzing the fluorescence intensities in the analysis regions A to F in such a manner that the images were analyzed in the image analysis device 50. Fluorescence intensity relative values are relative values of the fluorescence intensities in the analysis regions A to F in the case where the fluorescence intensity of the analysis region F is taken as "1". "Number of samples: n=10" stands for that microscope observation was performed for ten spots from among each of the regions of the analysis regions A to F in one sample slide.

Figure 24:
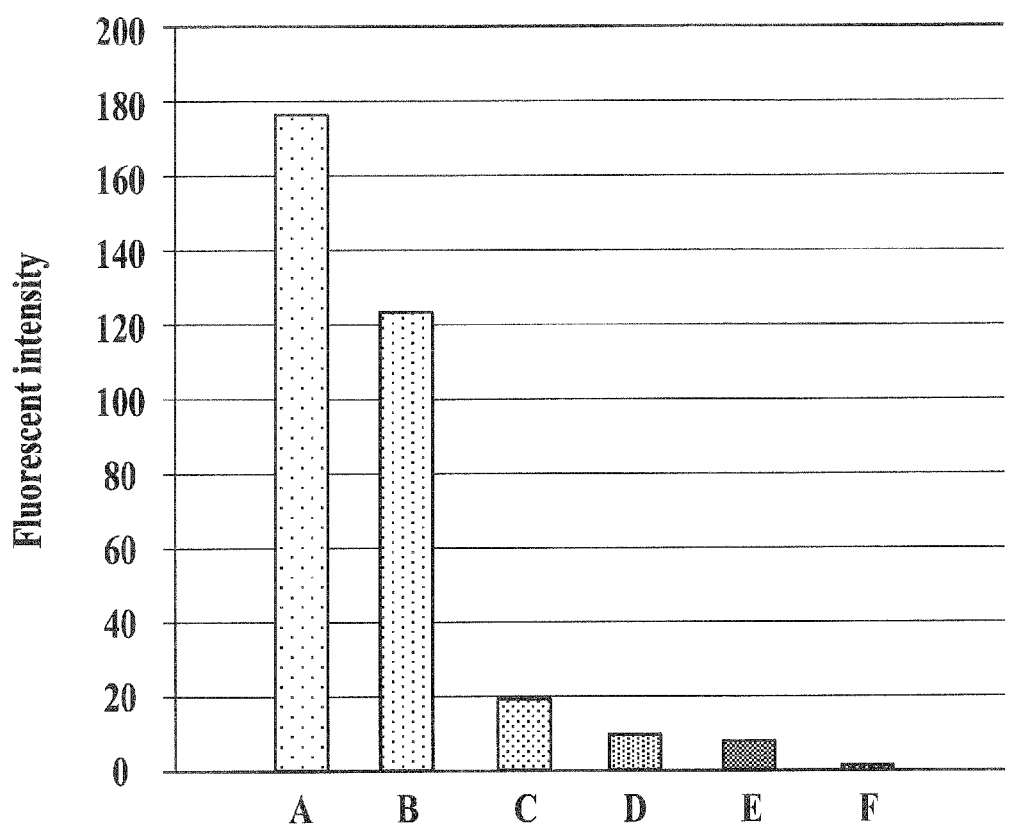
FIG. 24 is a graph showing fluorescence intensity relative values in the analysis regions A to F.

FIG. 24 is a graph of the fluorescence intensity relative values in the analysis regions A to F. In a similar way to FIG. 23, the fluorescence intensity of the analysis region F is taken as "1". By the quantitative evaluation for the fluorescence, it became possible to precisely evaluate the number of present quantum dots in each region in the inside of the sentinel lymph node.

Figure 25A:
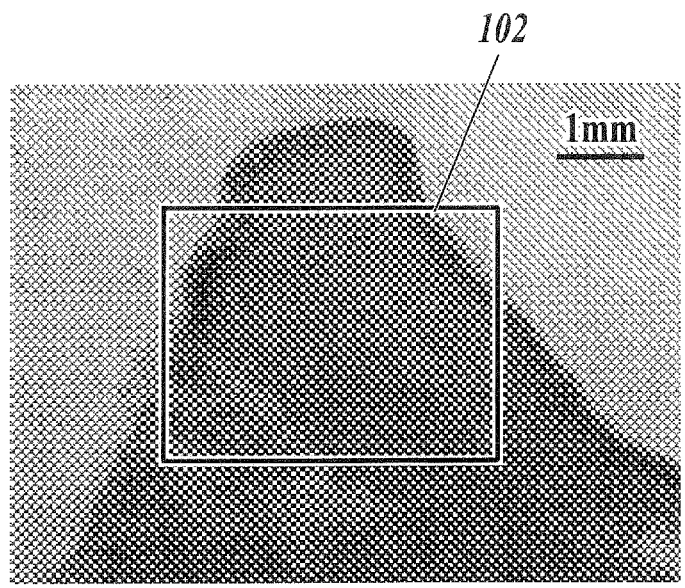
FIG. 25A is a microscope image of a sample in which a tissue of the sentinel lymph node is subjected to hematoxylin-eosin staining.
Figure 25B:
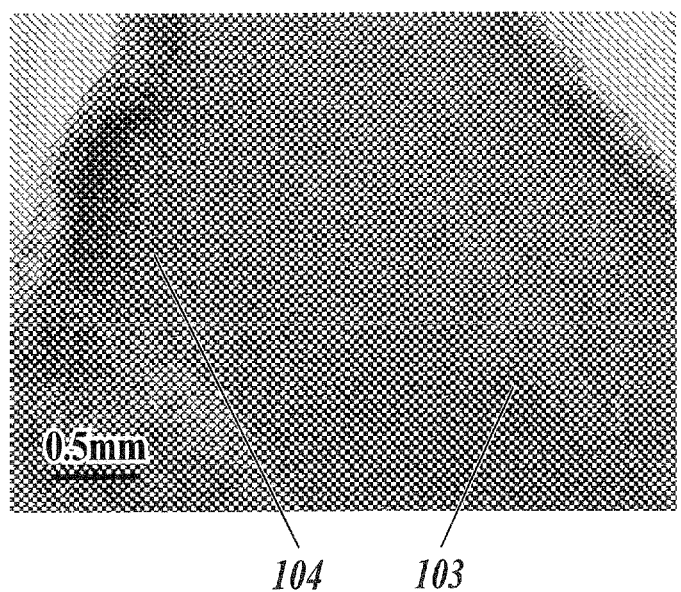
FIG. 25B is an image in which a part of FIG. 25A is enlarged.

FIG. 25A is a microscope image of a sample in which the tissue of the extirpated sentinel lymph node is subjected to the hematoxylin-eosin staining. A region 102 of FIG. 25A is a portion corresponding to a region 100 of FIG. 20A and a region 101 of FIG. 20B. FIG. 25B is an enlarged image of the region 102 of FIG. 25A. By the staining, positions of afferent lymph node vessel inflow regions 103 and 104 can be confirmed.

Figure 26A:
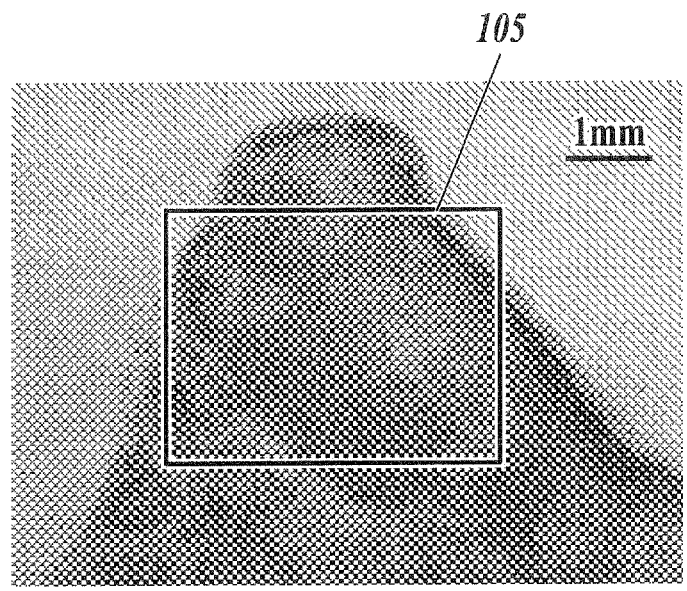
FIG. 26A is an immunostaining microscope image in which CD3 antibodies specific to T-cells in the lymph node are stained by DAB in the tissue of the sentinel lymph node.
Figure 26B:
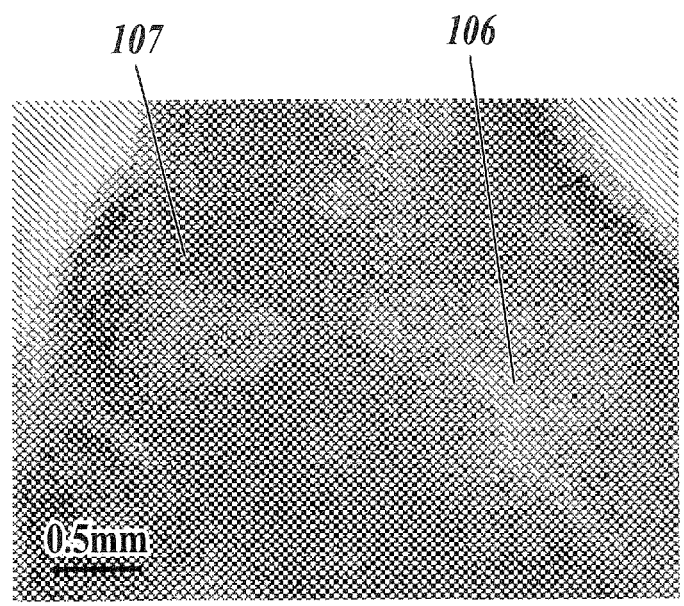
FIG. 26B is an image in which a part of FIG. 26A is enlarged.

FIG. 26A is an immunostaining microscope image in which CD3 antibodies specific to T-cells in the lymph node are stained by DAB in the tissue of the extirpated sentinel lymph node. A region 105 of FIG. 26A is a portion corresponding to the region 100 of FIG. 20A and the region 101 of FIG. 20B. FIG. 26B is an enlarged image of the region 105 of FIG. 26A. In FIG. 26B, portions surrounded by several lymph follicles which are not stained by the immunostaining are afferent lymph vessel inflow regions 106 and 107.

When consideration was made while combining the fluorescence analysis results shown in FIG. 21, FIG. 22A to FIG. 22F, FIG. 23 and FIG. 24 and the microscope analysis results shown in FIG. 25A, FIG. 25B, FIG. 26A and FIG. 26B, the regions (analysis regions A and B), each of which exhibited high fluorescence intensity in the sentinel lymph node, coincided with the vicinities of the afferent lymph vessel inflow regions.

That is to say, a large number of the quantum dots was present in the vicinities of the afferent lymph vessel inflow regions which receive the lymph flow from the injection portion of the quantum dots. Meanwhile, even in the same lymph node, the spots other than the afferent lymph vessel inflow regions did not exhibit so high fluorescence intensity as in the analysis regions A and B. Moreover, in the extirpated sentinel lymph node, other afferent lymph vessels than in the analysis regions A and B were also present, but did not exhibit the fluorescence. The other afferent lymph vessels were lymph vessels (other segments in the lymph node) which receive lymph flows from the gastric wall other than the injection portion of the quantum dots.

From the above, in the extirpated sentinel lymph node, the distribution of the quantum dots used as the tracer for the sentinel lymph node in the sentinel lymph node was quantitatively analyzed precisely, whereby it became possible to detect the afferent lymph vessel inflow regions in the sentinel lymph node. The vicinities of the afferent lymph vessel inflow regions are regions in which a risk of the cancer metastasis is high, and it is expected that, by the matter that the histopathological examination is concentratedly performed by taking as an index the data obtained by this fluorescence analysis method, detectability for the metastasis cancer cells in the sentinel lymph node will be remarkably enhanced.

<Antibody-Bonded Quantum Dots>

Next, observation was made for a difference (difference in behavior as the tracer) in localization of the quantum dots in the sentinel lymph node between the case of singly using the quantum dots as the tracer for the sentinel lymph node and the case of simultaneously using antibody-bonded quantum dots to which antibodies specific to certain cells are bonded.

As the tracer for the sentinel lymph node, not only the quantum dots (fluorescence wavelength: 705 nm) but also quantum dots (fluorescence wavelength: 605 nm) to which CD3 antibodies specific to cells (here, T-lymphocytes) present in the lymph node were bonded were simultaneously used, and a difference in behavior therebetween was observed. The quantum dots (CD3ab-QD) to which the CD3 antibodies are bonded and the quantum dots are different in fluorescence wavelength from each other, and even in the case of the same wavelength excitation (532 nm), an absorption filter of the microscope is just changed, whereby it is possible to evaluate the fluorescence intensity separately by the respective fluorescence wavelengths.

As a result, in a similar way to the case of singly using the quantum dots, the CD3ab-QD were localized in the afferent lymph vessel inflow regions of the sentinel lymph node, and in addition, were also present in the peripheries of T-cells as a target of the antibodies, and were capable of specifically marking the cells.

Figure 27A:
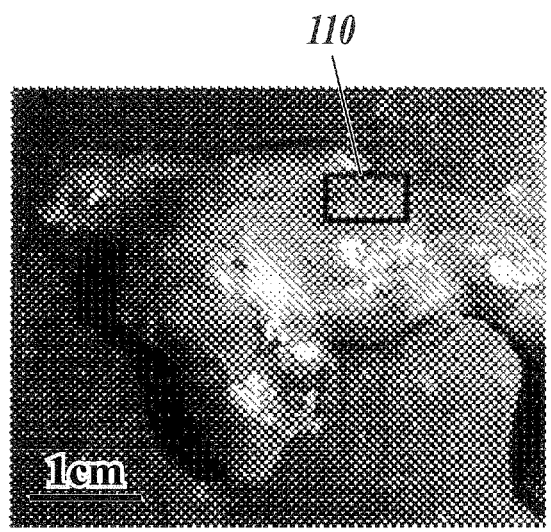
FIG. 27A is an imaged image of the sentinel lymph node.
Figure 27B:
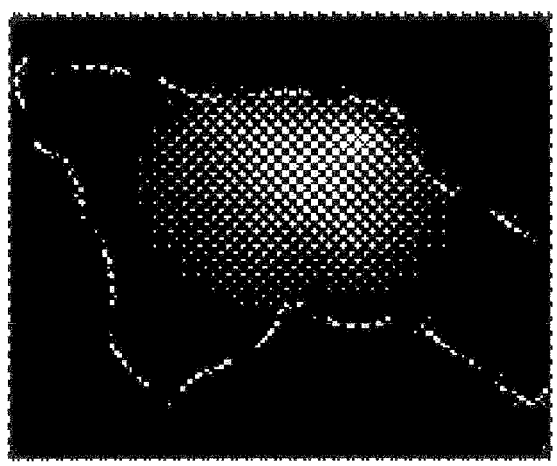
FIG. 27B is a fluorescence image of the sentinel lymph node.

FIG. 27A is an imaged image of the extirpated sentinel lymph node, and FIG. 27B is a fluorescence image of the same sentinel lymph node, which is acquired by the endoscope-type fluorescence measurement device 10.

Figure 27C:
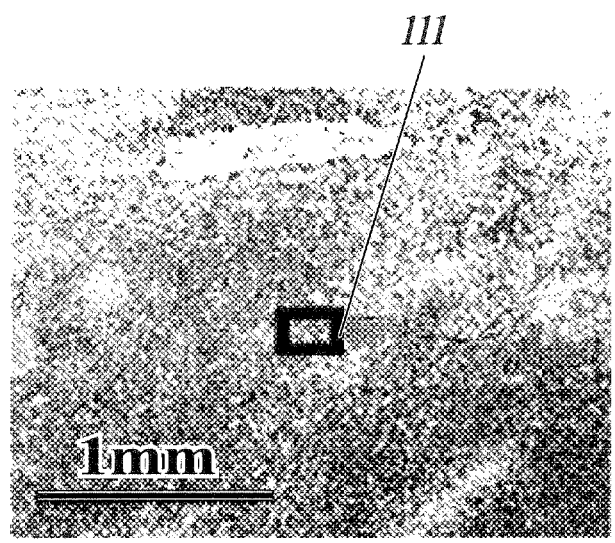
FIG. 27C is an immunostaining image of the sentinel lymph node.
Figure 27D:
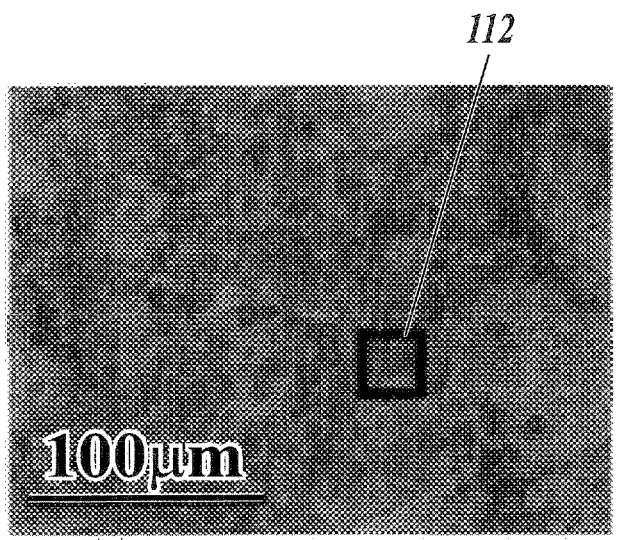
FIG. 27D is an immunostaining image of the sentinel lymph node.

FIG. 27C is an immunostaining image of a tissue of a region 110 in the imaged image of FIG. 27A, and FIG. 27D is an immunostaining image of a region 111 in FIG. 27C. In FIG. 27C and FIG. 27D, stained cells are the T-lymphocytes.

Figure 27E:
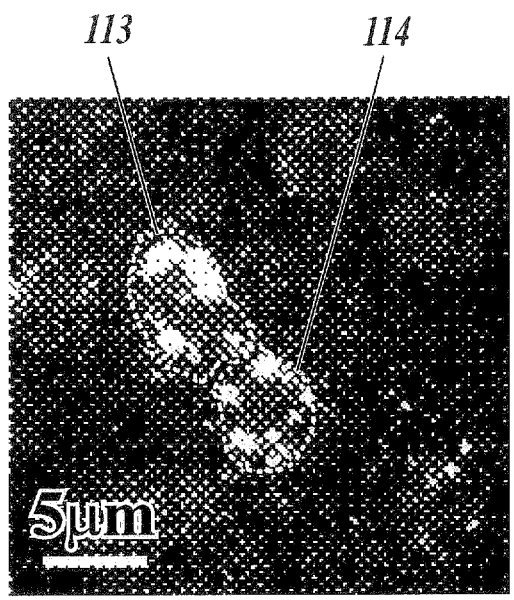
FIG. 27E is a fluorescence image in which a tissue of a region where many T-lymphocytes are present is imaged by an absorption filter for 605 nm.
Figure 27F:
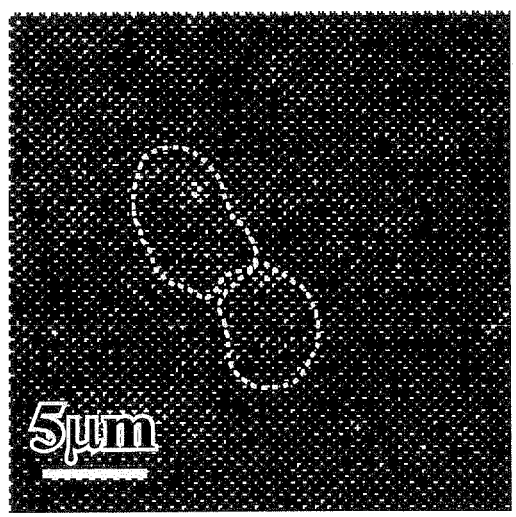
FIG. 27F is a fluorescence image in which the tissue of the region where many T-lymphocytes are present is imaged by an absorption filter for 705 nm.

FIG. 27E is a fluorescence image in which a tissue of a region 112 where many T-lymphocytes are present in FIG. 27D is subjected to the fluorescence analysis by the single-molecule fluorescence microscope 40 and the image analysis device 50, in which an absorption filter (band-pass filter for 565 to 625 nm) for 605 nm was used. Portions 113 and 114 corresponding to the T-lymphocytes exhibit the fluorescence. FIG. 27F is a fluorescence image in which the tissue of the region 112 where many T-lymphocytes are present in FIG. 27D is subjected to the fluorescence analysis by the single-molecule fluorescence microscope 40 and the image analysis device 50, in which an absorption filter (band-pass filter for 690 to 730 nm) for 705 nm was used. At a place where it was possible that a fixed amount of the quantum dots (705 nm) could be present in the vicinities of the lymph vessel inflow regions, it was confirmed that the CD3ab-Qd (605 nm) was localized in the peripheries of the T-lymphocytes, and marked the T-cells. As described above, the T-lymphocytes can be identified based on the fluorescence in the sentinel lymph node, and the detection accuracy for the T-lymphocytes can be enhanced.

By applying this method, a variety of tumor markers (antibodies) are bonded to the quantum dots, whereby it is possible to specifically mark cancer cells in the sentinel lymph node, and the internal structure analysis technology for the sentinel lymph node, which is developed by the inventors of the present invention, can be further advanced. That is to say, by using the quantum dots to which the antibodies specific to the cancer cells are bonded, the detection accuracy for the cancer cells can be enhanced.

<Detection Results of Sentinel Lymph Node>

FIG. 28 shows detection results of such sentinel lymph nodes. Specifically, FIG. 28 shows the respective body weights of six pigs, whether or not the fluorescence was detected at each injection portion, whether or not the fluorescence was detected at each lymph vessel, the number of sentinel lymph nodes, a time until the sentinel lymph nodes were detected. In all of experimental examples, it was possible to detect the sentinel lymph nodes within 10 minutes.

[Conclusion]

From the experimental results described above, it was confirmed that, in such a sentinel lymph node, the region where the fluorescence intensity was high, that is, the region where the quantum dots were localized was the afferent lymph vessel inflow regions. The lymph node metastasis of the cancer cells is considered to start from the vicinities of the afferent lymph vessel inflow regions, and accordingly, a metastasis starting region in the sentinel lymph node coincides with the localized region of the quantum dots in the sentinel lymph node. Hence, the distribution of the quantum dots in the sentinel lymph node is detected with high sensitivity/high accuracy, whereby it becomes possible to accurately detect the region where the risk of the cancer metastasis is high.

In accordance with the technique developed by the inventors of the present invention, the quantum dots can be used not only as the tracer for the sentinel lymph node, but also for the structure analysis for the sentinel lymph node by the single-molecule fluorescence microscope 40. The fluorescence intensity of the quantum dots in the sentinel lymph node is quantitatively evaluated with high accuracy, and the fluorescence distribution is finely analyzed, whereby the sentinel lymph node can be grasped as more precise microscopic areas in the lymph node. Specifically, by using the single-molecule fluorescence microscope 40 capable of the observation in the level of the single molecule, the fluorescence intensity is measured for each of the plurality of regions in the sentinel lymph node extirpated in the state where the quantum dots are injected thereinto, and one or plural regions are detected as the afferent lymph vessel inflow regions in order from one with the highest fluorescence intensity among the plural regions for which the measurement is performed. Hence, the regions in the sentinel lymph node, in each of which the fluorescence intensity is high, are detected as the afferent lymph vessel inflow regions. Accordingly, the regions in the sentinel lymph node, where it is possible that the metastasis cancer cells can be present, can be detected accurately.

Moreover, the images acquired by the single-molecule fluorescence microscope 40 are subjected to the image analysis in the image analysis device 50, whereby the fluorescence intensity can be accurately measured for each of the plural regions.

As described above, by taking as an index the fluorescence distribution of the quantum dots in the sentinel lymph node, it becomes possible to accurately take aim at the pathological diagnosis spot. The concentrated histopathological diagnosis is performed for the region where the risk of the metastasis is high, whereby false negative diagnosis (overlook of the cancer metastasis) is reduced, and it is expected that diagnosability will be remarkably enhanced. Moreover, it also becomes possible to minimize the number of sections necessary for the histopathological diagnosis.

Moreover, it has been exhibited that, in the event of performing the sentinel lymph node biopsy, the quantum dots to which the antibodies specifically reacting with the cells in the lymph node are bonded are used, whereby it is possible to impart activity destined to the target. By using the quantum dots to which the antibodies specifically reacting with the cancer cells are bonded, the presence of the cancer cells in the sentinel lymph node can be finally ascertained, and the detection accuracy for the cancer cells can be enhanced.

INDUSTRIAL APPLICABILITY

The method for detecting the afferent lymph vessel inflow regions and the method for identifying the specific cells according to the present invention have applicability in the medical field of detecting the regions where it is possible that the cancer cells can be present.

EXPLANATION OF REFERENCE NUMERALS

1 FLUORESCENCE MEASUREMENT SYSTEM
2 MICROSCOPE SYSTEM
10 ENDOSCOPE-TYPE FLUORESCENCE MEASUREMENT DEVICE
11 EMCCD CAMERA
12 LENS
13 FLUORESCENCE FILTER
14 LIGHT GUIDE
15 ENDOSCOPE UNIT
16 HANDLE
20 IMAGE ANALYSIS DEVICE
21 CPU
22 ROM
23 RAM
24 COMMUNICATION UNIT
25 OPERATION UNIT
26 DISPLAY UNIT
27 STORAGE UNIT
28 BUS
30 LASER BEAM EXCITATION DEVICE
40 SINGLE-MOLECULE FLUORESCENCE MICROSCOPE
50 IMAGE ANALYSIS DEVICE
51 CPU
52 ROM
53 RAM
54 COMMUNICATION UNIT
55 OPERATION UNIT
56 DISPLAY UNIT
57 STORAGE UNIT
58 BUS

The invention claimed is:

1. A method for detecting afferent lymph vessel inflow regions, the method comprising:
injecting a predetermined amount of 15-20 nm quantum dots into a patient;
detecting a fluorescence of the quantum dots in a sentinel lymph node of the patient;
extirpating the sentinel lymph node;
measuring a fluorescence intensity of the quantum dots for each of a plurality of regions in the extirpated sentinel lymph node using a sinqie-molecule confocal fluorescence microscope; and
detecting from the plurality of regions of the extirpated sentinel lymph node, a higher quantum dot fluorescence intensity than other regions of the extirpated. sentinel lymph node, wherein the regions having significantly hit. her quantum dot fluorescence intensity in the extirpated sentinel lymph node provides detection of the afferent lymph node vessel inflow regions.

2. The method for detecting afferent lymph vessel inflow regions according to claim 1,
wherein the fluorescence intensity is measured by obtaining an image of each of the plurality of regions in the sentinel lymph node with the single-molecule confocal fluorescence microscope; and
performing an image analysis for each of the image obtained.

3. The method for detecting afferent lymph vessel inflow regions according to claim 2,
wherein the quantum dots include quantum dots to which antibodies that specifically bind to specific cells are bonded to label the specific cells, and
the specific cells are identified based on their quantum dot fluorescence intensity in the sentinel lymph node.

4. The method for detecting afferent lymph vessel inflow regions according to claim 3,
wherein the specific cells are T-lymphocytes.

5. The method for detecting afferent lymph vessel inflow regions according to claim 3,
wherein the specific cells are cancer cells.

6. The method for detecting afferent lymph vessel inflow regions according to claim 1,
wherein the quantum dots include quantum dots to which antibodies that specifically bind to specific cells are bonded to label the specific cell, and
the specific cells are identified based on their quantum dot fluorescence intensity in the sentinel lymph node.

7. The method for detecting afferent lymph vessel inflow regions according to claim 6,
wherein the specific cells are T-lymphocytes.

8. The method for detecting afferent lymph vessel inflow regions according to claim 6,
wherein the specific cells are cancer cells.

9. A method for detecting afferent lymph vessel inflow regions, the method comprising:
injecting a predetermined amount of 15-20 nm quantum dots into a patient;
detecting a fluorescence of the quantum dots in a sentinel lymph node of the patient;
extirpating the sentinel lymph node;
measuring a fluorescence intensity of the quantum dots for each of a plurality of regions in the extirpated sentinel lymph node; and
detecting from the plurality of regions of the extirpated sentinel lymph node, a higher quantum dot fluorescence intensity than other regions of the extirpated sentinel lymph node, wherein the regions having significantly higher quantum dot fluorescence intensity in the extirpated sentinel lymph node provides detection of the afferent lymph node vessel inflow regions,
wherein the quantum dots include quantum dots to which antibodies that specifically bind to specific cells are bonded to label the specific cell, and
the specific cells are identified based on their quantum dot fluorescence intensity in the sentinel lymph node.

10. The method for detecting afferent lymph vessel inflow regions according to claim 9,
  wherein the specific cells are T-lymphocytes.

11. The method for detecting afferent lymph vessel inflow regions according to claim 9,
  wherein the specific cells are cancer cells.

12. The method, for detecting afferent lymph vessel inflow regions according to claim 9,
  wherein the fluorescence intensity is measured by obtaining an image of each of the plurality of regions in the sentinel lymph node with a confocal fluorescence microscope; and performing an image analysis for each of the image obtained, and
  wherein the quantum dots include quantum dots to which antibodies that specifically bind to specific cells are bonded to label the specific cells, and
  the specific cells are identified based on their quantum dot fluorescence intensity in the sentinel lymph node.

13. The method for detecting afferent lymph vessel inflow regions according to claim 12,
  wherein the specific cells are T-lymphocytes.

14. The method for detecting afferent lymph vessel inflow regions according to claim 12,
  wherein the specific cells are cancer cells.

15. The method for detecting afferent lymph vessel inflow regions according to claim 12, wherein the confocal fluorescence microscope provides detection of a single molecule.

* * * * *